US007341994B2

(12) United States Patent
Ishikawa et al.

(10) Patent No.: US 7,341,994 B2
(45) Date of Patent: Mar. 11, 2008

(54) GD3-MIMETIC PEPTIDES

(75) Inventors: Dai Ishikawa, Tokushima (JP); Koichi Ogino, Tokushima (JP); Takao Taki, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 839 days.

(21) Appl. No.: 10/257,950

(22) PCT Filed: Apr. 23, 2001

(86) PCT No.: PCT/JP01/03443

§ 371 (c)(1),
(2), (4) Date: Oct. 23, 2002

(87) PCT Pub. No.: WO01/81371

PCT Pub. Date: Nov. 1, 2001

(65) Prior Publication Data

US 2006/0058226 A1 Mar. 16, 2006

(30) Foreign Application Priority Data

Apr. 25, 2000 (JP) ............................. 2000-124259

(51) Int. Cl.
*A61K 38/17* (2006.01)
*C07K 14/82* (2006.01)
(52) U.S. Cl. ........................ 514/12; 514/14; 530/387.5; 530/387.9
(58) Field of Classification Search ................... 514/14; 530/387.5, 387.9
See application file for complete search history.

(56) References Cited

U.S. PATENT DOCUMENTS 5,102,663 A 4/1992 Livingston et al.
6,676,946 B2 * 1/2004 Bay et al. .............. 424/196.11

FOREIGN PATENT DOCUMENTS

| EP | 533 199 | 3/1993 |
| JP | 8-53366 | 2/1996 |
| JP | 8-508978 | 9/1996 |
| JP | 10-237098 | 9/1998 |
| JP | 10-237099 | 9/1998 |

OTHER PUBLICATIONS

Qui et al (Hybridoma 18:103-112 (1999)).*
Monzavi-Karbassi et al. (TRENDS in Biotech. 20(5):207-214 (May 2002)).*
Hakomori (Adv Exp Med Biol 491:369-402 (2001)).*
Willers et al (Peptides 20:1021-1026 (1999)).*
Burgess et al, Journal of Cell Biology vol. 111 Nov. 1990 2129-2138).*
Lazar et al Molecular and Cellular Biology Mar 1988 vol. 8 No. 3 1247-1252).*
Lin et al Biochemistry USA vol. 14:1559-1563 (1975).*
Schwartz et al, Proc Natl Acad Sci USA vol. 84:6408-6411 (1987).*
Stedman's Medical Dictionary 27th Ed.*
Popa et al., FEBS Letters 580:1398-1404, 2006.*
Worley, K.C. (ref 2, submitted Aug. 4, 2000; see copy of search output, pp. 1-2).*
Cerato et al. (Hybridoma 16(4):307-316 (1997).*
AC078804 NCBI Blast report (pp.1-12).*
Lederman et al (Molecular Immunology 28:1171-1181, 1991).*
Li et al (Proc. Natl. Acad. Sci. USA 77:3211-3214, 1980).*
Jianping Qiu et al.: "Toward the development of peptide mimotopes of carbohydrate antigens as cancer vaccines" HYBRIDOMA, vol. 18, No. 1, pp. 103-112 1999.
Soo Kie Kim et al.: "Comparison of the effect of different immunological adjuvants on the antibody and T-cell response to immunization with MUC1-KLH" VACCINE, vol. 18, pp. 597-603 Hybridoma (1), (1999) 2000.
David A. Cheresh et al.: "Localization of gangliosides $GD_2$ and $GD_3$ in adhesion plaques and on the surface of human melanoma cells" Proc. Natl. Acad. Sci., vol. 81, pp. 5767-5771 Sep. 1984.
Meenhard Herlyn et al.: "Characteristics of cultured human melanocytes isolated from different stages of tumor progression" Cancer Research, vol. 45, pp. 5670-5676 Nov. 1985.
Alan N. Houghton et al.: "Mouse monoclonal $IgG_3$ antibody detecting $G_{D3}$ ganglioside: A phase I trial in patients with malignant melanoma" Proc. Natl. Acad. Sci., vol.82, p. 1242-1246 Feb. 1985.
Philip O. Livingston: "Approaches to augmenting the immunogenicity of melanoma gangliosides: From whole melanoma cells to ganglioside_KLH conjugate vaccines" Immunological Review, vol. 145, pp. 147-163 1995.
Philip O. Livingston et al: "Carbohydrate vaccines that induce antibodies against cancer. 1 Rationale" Cancer Immunol. Immunother., vol. 45, pp. 1-45 1997.
Charlotte R. Kensil et al.: "Separation and characterization of saponins with adjuvant activity from Quillaja saponaria molina cortex" J. Immunol., vol. 146, No. 2, pp. 431-437 Jan. 15, 1991.
Dai Ishikawa et al.: "Preparation of glycol-replica peptides" Cell Enginerring, vol. 16, No. 12, pp. 1821-1828 1997.
Jianping Qiu et al.: "Towards the development of peptide mimotopes of carbohydrate antigens as cancer vaccines" HYBRIDOMA, vol. 18, No. 1, pp. 103-112 1999.
Joerg Willers et al.: "Molecular mimicry of phage displayed peptides mimicking GD3 ganglioside" PEPTIDES, vol. 20, pp. 1021-1026 1999.
Jorg Willers, et al., "Molecular mimicry of phage displayed peptides mimicking GD3 ganglioside", PEPTIDES, vol. 20, No. 9, pp. 1021-1026 1999.

(Continued)

*Primary Examiner*—Larry R. Helms
*Assistant Examiner*—Lynn Bristol
(74) *Attorney, Agent, or Firm*—Oblon, Spivak, McClelland, Maier & Neustadt, P.C.

(57) ABSTRACT

GD3-Mimetic peptides which contain an amino acid sequence represented by any of SEQ ID NOS: 1 to 4 or an amino acid sequence derived therefrom by substitution, deletion, addition, or insertion of one or more amino acid residues and attaining specific binding to an anti-GD3 antibody; and medicinal compositions containing the same.

2 Claims, 8 Drawing Sheets

OTHER PUBLICATIONS

Dai Ishikawa, et al., "GD1α-replica peptides functionally mimic GD1α, an adhesion molecule of metastatic tumor cells, and suppress the tumor metastasis", FEBS Letters, vol. 441, No. 1, pp. 20-24 Dec. 11, 1998.

Jamie K. Scott, et al., "Searching for peptide ligands with an epitope library", SCIENCE, vol. 249, pp. 386-390 1990.

Thomas Kieber-Emmons, et al., "Vaccination with carbohydrate peptide mimotopes promotes anti-tumor responses", Nature Biotechnology, vol. 17, No. 7, pp. 660-665 1999.

Friedhelm Helling, et al., "GD3 Vaccines for melanoma: superior immunogenicity of keyhole limpet hemocyanin conjugate vaccines", Cancer Research, vol. 54, pp. 197-203 Jan. 1, 1994.

M. Laura Nasi, et al. "Anti-melanoma effects of R24, a monoclonal antibody against GD3 ganglioside", Melanoma Research, vol. 7, No. suppl. 2, pp. S155-S162 1997.

Philip O. Livingston, "Approaches to augmenting the immunogenicity of melanoma gangliosides: from whole melanoma cells to ganglioside-KLH conjugate vaccines", Immunological Reviews, No. 145, pp. 147-166 1995.

Kim et al. "Comparison of the effect of different immunological adjuvants on the antibody and T-cell response to immunization with MUC1-KLH and GD3-KLH conjugate cancer vaccines", Vaccine, vol. 18, pp. 597-603 2000.

* cited by examiner

Fig. 2

```
                          GD3R1N9
                        ┌──────────┐
GD3R1          LAPPRPRSELVFLSV
                        └──────────┘
                            GD3R1C9

GD3R2          PHFDSLLYPCELLGC

GD3R3N9
                      ┌──────────┐
GD3R3          GLAPPDYAERFFLLS
                      └──────────┘
                          GD3R3C9
                    GD3R4N9
                  ┌──────────┐
GD3R4          RHAYRSMAEWGFLYS
                      └──────────┘
                          GD3R4C9
```

GD3-MIMETIC PEPTIDES

TECHNICAL FIELD

The present invention relates to GD3-mimetic peptides, and more particularly to novel peptides which are considered to structurally mimic GD3, which are known as tumor associated antigens found in tumors such as melanoma.

BACKGROUND ART

GD3 is one form of sialosyl sphingoglycolipids; G stands for ganglioside (sialosyl sphingoglycolipid) and D stands for disialo. GD3, like other tumor-associated antigens such as GM2, GM3, GD2, and GT3, is known to be expressed on tumor cells such as those of human melanoma. The structural formula of GD3 is represented by NeuAc α2-8 NeuAc α2-3 Gal β1-4 Glc β1-1 Cer.

Previous reports regarding GD3 have revealed, among other findings, that development of a tumor correlates to expression of GD3, that GD3 is highly expressed on melanoma cells, and that administration of mouse anti-GD3 monoclonal antibody suppresses growth of tumors of melanoma patients. On the basis of these findings, GD3 has become of keen interest in immunotherapy of these types of tumors.

Thus, human immune response against GD3 is expected to provide beneficial effects during the clinical course of pathological conditions; in fact, a variety of clinical tests have been performed in the technical field of vaccines. However, successful results that fulfill the above expectation have yet not been reported (see, for example, Cheresh, D. A., et al., Proc. Natl. Acad. Sci., USA., 81, 5767-5771 (1984): Herlyn, M., et al., Cancer Res., 45, 5670-5676 (1985): Houghton, A. N., et al., Proc. Natl. Acad. Sci., USA., 82, 1242-1246 (1985): Livingston, P. O., Immunological Rev., 145, 147-163 (1995): Livingston, P. O., et al., Cancer Immunol. Immunother., 45, 1-9 (1997)).

Gangliosides, which have been found to be associated with tumors, are thus known to serve as a useful target in the immunological attack against cancer. However, they are acknowledged to have poor immunogenicity.

In order to overcome this drawback, there has been developed and disclosed a cancer vaccine composition for inducing or stimulating immune response of antibodies against gangliosides (Japanese Patent Application Laid-Open (kokai) No. 8-53366). This composition is an N-glycosylated product of ganglioside (i.e., N-glycosyl GM3).

Similarly, U.S. Pat. No. 5,102,663 discloses a 9-O-acetylated product of ganglioside (9-O-acetylated GD3).

Moreover, Japanese Kohyo Publication No. 8-508978 discloses that a similar cancer vaccine, GD3 complex vaccine (GD3-keyhole limpet hemocyanin complex), exhibits significantly improved antibody responses. According to the disclosure of this publication, a double bond in the ceramide backbone of GD3 are cleaved with ozone for chemical modification, thus introducing an aldehyde group, and the aldehyde group is caused to bind to the aminolysyl group of protein through reductive amination, to thereby construct a complex with a synthesized multi-antigenic peptide displaying repeats of malarial T cell epitopes, coat protein of *Neisseria meningitidis* (OMP), cationized bovine serum albumin (cBSA), keyhole limpet hemocyanin (KLH) and polylysin. That publication also describes that the most effective immunological adjuvant is QS-21, obtained through extraction of the bark of a tree found in South America and called *Quillajasaponaria Molina* (Aquila Pharmaceuticals, Worcester, Mass., U.S.A.: Kensil, C. R. et al., J. Immunol., 146, 431 (1991)).

Conventional vaccines prepared through employment of GD3 per se as an antigen exhibit only weak immune responses and their effects are transient. Moreover, they have drawbacks, in that the raw material GD3 is not readily available. That is, generally speaking, mass production of a desired ganglioside from a living organism is very difficult. Also, synthesis of a ganglioside through chemical synthesis or genetic engineering is very difficult.

When vaccines are prepared through a variety of chemical modifications of GD3, particularly in chemical treatment performed for improving antigenicity or in preparation of complexes, disadvantages are encountered in terms of intricate procedure in relation to procurement, preparation, synthesis, etc. of raw materials for antigens and complexes, and necessity for selection of immunoadjuvants.

Meanwhile, in recent years, molecular biological techniques have been employed in the technical fields of complex saccharides, and techniques for replacing the sugar chain with peptide are now under development. Previously, the present inventors have successfully obtained, from a phage display random peptide library through biopanning using a monoclonal antibody against a sugar chain, a peptide which exhibits specific binding to an antibody against one form of ganglyoside, GD1α.

This peptide (15 mer) has been found to mimic the sugar chain structure of a complex glycolipid (and thus is called a glyco-replica peptide), to be bound, with specificity to, a monoclonal antibody against glycolipid GD1α, and to inhibit binding of an antibody to antigen GD1α.

The present inventors have also produced this peptide through chemical synthesis, and have confirmed that the peptide reacts with a monoclonal antibody for GD1α, that a (chemically synthesized) replica peptide of GD1α inhibits cell adhesion of cancer cells of highly metastatic cancer cell lines, and that the replica peptide inhibits metastasis of cancer cells (Japanese Patent Application Laid-Open (kokai) No. 10-237099).

In addition, the present inventors have succeeded in obtaining, from a random peptide library, a peptide which exhibits to modulate glycosidase activity and reacts with specificity with an antibody against lactotetraosyl ceramide or lactoneotetrasyl ceramide (see Japanese Patent Application Laid-Open (kokai) No. 10-237098 and Saibo Kogaku, Dai Ishikawa and Takao Taki, 16 (12) 1821-1828 (1997)).

A recently published report discloses study results similar to the above-described ones obtained by the present inventors. Specifically, Qiu, J., et al. have disclosed in Hybridoma 18(1) 103-112 (1999) that a 15-16 mer peptide containing a Trp-Arg-Tyr sequence and obtained from a phage display peptide library through use of an antibody against a GD2/GD3 antigen exhibits cross reaction with the antibody.

Willers, J., et al. describe that they have obtained, from two phage display peptide libraries of phages displaying 15-mer and 8-mer peptides, four phage-displayed peptides capable of binding to anti-GD3 monoclonal antibodies MB3.6, MG22, and MG21 (Peptides, 20, 1021-1026 (1999)). According to this publication, these peptides were found to exhibit ability to binding to the anti-GD3 antibody employed for selection, and this binding ability was inhibited by GD3, but desired immunogenicity was not observed for any of the peptides.

An object of the present invention is to provide a novel peptide which mimics the structure of the sugar chain of ganglioside GD3 and exhibits high affinity with anti-GD3 antibody.

Another object of the present invention is to provide an immunogenic peptide capable of producing GD3-specific antibody; in particular, a peptide having a characteristic feature such that an antibody produced through immunization with an immunogen comprising the peptide cross-reacts with GD3, and therefore, has utility as a vaccine which replaces GD3.

A still further object of the present invention is to provide a DNA sequence coding for the above-mentioned peptide, a recombinant expression vector in which the sequence has been integrated, a host cell harboring the vector, and a recombinant expression product produced by the cell.

A still further object of the present invention is to provide a pharmaceutical composition containing as an active ingredient the above-mentioned peptide or the recombinant expression vector.

DISCLOSURE OF THE INVENTION

The present inventors have carried out extensive studies, and have found a novel amino acid sequence exhibiting high affinity to an anti-GD3 antibody. The inventors have also found that an antiserum obtained through immunization with a GD3-mimetic peptide comprising a peptide containing the amino acid sequence exhibits cross-reactivity with GD3, and that the GD3-mimetic peptide finds utility as a vaccine that replaces GD3. The present invention has been accomplished on the basis of these findings.

Accordingly, the present invention provides a GD3-mimetic peptide containing an amino acid sequence represented by any one of SEQ ID NOs: 1 to 4 or an amino acid sequence derived therefrom by substitution, deletion, addition, or insertion of one or more amino acid residues and exhibiting binding specificity to an anti-GD3 antibody.

In particular, the present invention provides a GD3-mimetic peptide which is in a fused form of peptide—fused with a carrier protein capable of enhancing immunogenicity—and the GD3-mimetic peptide, wherein the carrier protein is keyhole limpet hemocyanin; a multi-antigenic GD3-mimetic peptide containing at least one species of the GD3-mimetic peptide; an immunogenic GD3-mimetic peptide having the ability to produce a GD3-specific antibody; and a GD3-mimetic peptide having an amino acid sequence represented by any one of SEQ ID NOS: 1 to 4.

The present invention also provides a pharmaceutical composition containing, as an active ingredient, the GD3-mimetic peptide.

The present invention encompasses, among others, the following embodiments:

(1) a DNA sequence encoding the GD3-mimetic peptide of the present invention, particularly a DNA sequence encoding an amino acid sequence represented by any one of SEQ ID NOS: 1 to 4, preferably an amino acid sequence represented by SEQ ID NO: 3 or 4;

(2) a DNA sequence as described above, having a DNA sequence represented by any one of SEQ ID NOS: 5 to 8;

(3) a recombinant expression vector into which at least one of these DNA sequences has been inserted;

(4) a host cell into which the above recombinant expression vector has been incorporated;

(5) a pharmaceutical composition containing, as an active ingredient, the recombinant expression vector;

(6) use of the pharmaceutical composition of the present invention as a vaccine for stimulating induction of an antibody capable of recognizing GD3 or for enhancing production of the antibody;

(7) use of the pharmaceutical composition of the present invention as a drug for suppressing a tumor or cancer or for inhibiting cancerous metastasis;

(8) use of the drug for treating GD3-expressing tumors or cancer, particularly pathological conditions selected from the group consisting of melanoma, cancer of the large intestine, ovarian cancer, liver cancer, breast cancer, brain tumor, kidney cancer, pancreas cancer, cervical cancer, esophageal cancer, lung cancer, and stomach cancer; and (9) a pharmaceutical composition which is a liposome drug preparation.

As used herein, abbreviations for amino acids, peptides, nucleotide sequences, nucleic acids, etc. are in accordance with the IUPAC standards; IUB standards; "Guidelines for Drafting Specifications or Similar Materials Containing a Nucleotide Sequence or an Amino Acid Sequence," (edited by Japanese Patent Office); and symbols customarily employed in the art.

BRIEF DESCRIPTION OF THE DRAWINGS

FIG. 2 shows sequences of multi-antigenic peptides (SEQ ID NOS:1-4) employed in Example 5.

BEST MODES FOR CARRYING OUT THE INVENTION

Figure 1:
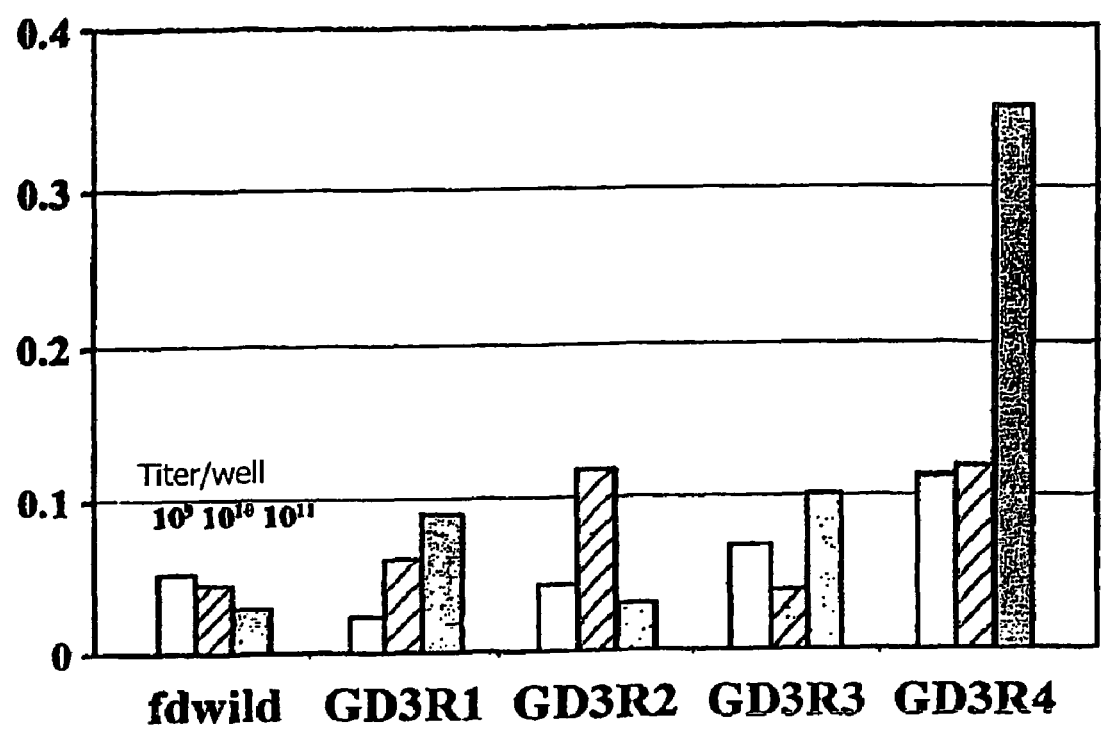
FIG. 1 is a graph showing binding affinity, as determined through the method described in relation to Example 2, of the immunogenic peptides according to the present invention and anti-GD3 antibody.

The GD3-mimetic peptides of the present invention will next be described in detail.

The GD3-mimetic peptides of the present invention are characterized by containing an amino acid sequence represented by any one of SEQ ID NOS: 1 to 4 or an amino acid sequence derived therefrom by substitution, deletion, addition, or insertion of one or more amino acid residues and being capable of binding to an antibody to GD3 (anti-GD3 antibody) with specificity.

As used herein, "anti-GD3 antibody" is a term generally employed in the art and is defined as a specific antibody capable of recognizing GD3 (i.e., binding to GD3). The antibody preferably exhibits no cross reactivity with other gangliosides relating to GD3 and is particularly preferably a monoclonal antibody.

The amino acid sequence represented by any one of SEQ ID NOS: 1 to 4 is characterized by mimicking the sugar chain structure of GD3. Thus, a peptide containing the amino acid sequence, exhibiting specific binding to an anti-GD3 antibody, is a preferred example of the GD3-mimetic peptides of the present invention.

The aforementioned specific amino acid sequence may be an amino acid sequence derived through modification of a portion of amino acid residues or a portion of the sequence, so long as the structural feature; i.e., mimicking the sugar chain structure of GD3, is maintained or presented.

No particular limitation is imposed on the extent and position of the modification (i.e., substitution, deletion, addition, or insertion) of the amino acid sequence, so long as the modified amino acid sequence is an equivalent in terms of effect and exhibits characteristics similar to those of the amino acid sequence represented by any one of SEQ ID NOS: 1 to 4; i.e., mimicking the sugar chain structure of GD3, is maintained or presented.

Modification may be generally effected to an extent of 80% or more homology, preferably 90% or more homology.

Among the peptides falling within the scope of the present invention, a peptide having at least two cysteine residues; e.g., a peptide having an amino acid sequence represented by SEQ ID NO: 2, is considered to spontaneously cyclize. Such a cyclic peptide is active (exhibits specific binding to an anti-GD3 antibody) even when the peptide is present in a linear-chain form. Therefore, one or both cysteine residues included in the peptide or an amino acid sequence portion sandwiched by these two cysteine residues can be deleted without greatly affecting the structural characteristics of mimicking the sugar chain structure of GD3. This phenomenon is supported by the literature (e.g., Koivunen, et al., J. Biol. Chem., 268, 20205-20210 (1993)).

Examples of the aforementioned deleted amino acid sequence include a sequence of nine amino acid residues (PHFDSLLYP-SEQ ID NO:16) residing in the N-terminus of GD3R2.

Any of the GD3-mimetic peptides of the present invention is formed of a peptide containing one of the aforementioned specific amino acid sequences falling within the scope of the present invention. Thus, the structural characteristic; i.e., mimicking the sugar chain structure of GD3, is maintained or presented, and the GD3-mimetic peptide is characterized by specific binding to an anti-GD3 antibody.

From the viewpoint of immunogenicity and other properties, the aforementioned peptides containing any one of the specific amino acid sequences has a number of amino acid residues of at least 5, preferably 8 to 60, more preferably 8 to 30, still more preferably 10 to 20.

The GD3-mimetic peptides of the present invention preferably have an amino acid sequence represented by SEQ ID NO: 3 or 4, particularly preferably an amino acid sequence represented by SEQ ID NO: 4. Alternatively, the GD3-mimetic peptides preferably have an amino acid sequence derived from an amino acid sequence represented by SEQ ID NO: 3 or 4 by substitution, deletion, addition, or insertion of one or more amino acid residues.

More preferably, the GD3-mimetic peptides of the present invention are immunogenic peptides which are capable of producing a GD3-specific antibody. In other words, the peptides can induce a GD3-specific antibody.

Specifically, the GD3-mimetic peptides of the present invention, which are characterized by containing an amino acid sequence represented by any one of SEQ ID NOS: 1 to 4, per se have the ability to produce a GD3-specific antibody, and therefore, such peptides are preferred as the immunogenic peptides of the present invention.

The immunogenic peptides of the present invention also encompass peptides which become to have a desired immunogenicity through transformation into immunogenicity-enhanced forms, as well as peptides of the immunogenicity-enhanced forms.

Thus, the immunogenic peptides having ability to produce a GD3-specific antibody, which peptides are preferred embodiments of the present invention, encompass the unmodified peptides per se and immunogenicity-enhanced forms of the GD3-mimetic peptides such as a form of a peptide fused with a customary carrier protein for enhancing immunogenicity and a form of a multi-antigen peptide, these two forms falling within the scope of the present invention.

Whether the GD3-mimetic peptides of the present invention maintain or present the structural characteristic of mimicking the sugar chain structure of GD3 (i.e., exhibit specific binding to an anti-GD3 antibody) can be confirmed by checking reactivity with the anti-GD3 antibody through a routine test method. In addition, whether the GD3-mimetic peptides of the present invention are immunogenic peptides having the ability to produce a GD3-specific antibody can be confirmed by checking, through a routine test method, cross reactivity of induced antibodies with GD3.

Detection of binding specificity of the GD3-mimetic peptides of the present invention to an anti-GD3 monoclonal antibody and reactivity of GD3 with an antibody induced by an immunogenic peptide will be specifically described in the below-described Examples.

The GD3-mimetic peptides of the present invention encompass the following embodiments.

(a) a GD3-mimetic peptide comprising a peptide containing an amino acid sequence formed through fusion or linkage of a plurality of members of at least one species of the aforementioned specific amino acid sequences;

(b) a GD3-mimetic peptide in a multi-antigen peptide form comprising a peptide containing at least one species of the aforementioned specific amino acid sequence; and (c) a GD3-mimetic peptide in a fusion peptide form, fused with a carrier protein or a peptide which can enhance imunogenicity or promote immune response.

These specific examples of the GD3-mimetic peptides of the present invention will next be described in more detail.

In the below-described Examples, peptides represented by GD3R1, GD3R2, GD3R3, and GD3R4 denote peptides having amino acid sequences represented by SEQ ID NOS: 1 to 4, respectively. These peptides are preferred examples of the GD3-mimetic peptides of the present invention. Peptides formed of arbitrarily continuous 9 to 14 amino acid residues contained in an amino acid sequence represented by any one of SEQ ID NOS: 1 to 4 are also preferred. Of these, peptides formed of 9 to 14 N-terminus or C-terminus amino acid residues contained in an amino acid sequence represented by any one of SEQ ID NOS: 1 to 4 are more preferred. Peptides formed of nine N-terminus or C-terminus amino acid residues contained in an amino acid sequence represented by any one of SEQ ID NOS: 1 to 4 are particularly preferred. As shown in Examples, these peptides were obtained by selecting peptides exhibiting specific binding to an anti-GD3 antibody by use of phage display libraries.

The screening step is not necessarily repeated for producing the GD3-mimetic peptides of the present invention. If desired, screening is performed, for example, in the following manner.

Specifically, a large population of molecules (library) are produced, and peptides of interest are identified through screening the molecule library. A phage display library can be employed for screening. The method for producing the library and screening method are disclosed in the literature (e.g., Scott, J. M. and Smith, G. P., Science, 249, 386-390 (1990); Smith, G. P. and Scott, J. K., Methods in Enzymology, 217, 228-257 (1993)). Examples of preferable methods for identifying the GD3-mimetic peptides of the present invention include methods for identifying glycolipid sugar chain-mimetic peptides disclosed in, for example, Japanese Patent Application Laid-Open (kokai) Nos. 10-237099 and 10-237098, and Dai ISHIKAWA and Takao TAKI, Cell Engineering, 16 (12) 1821-1828 (1997).

Phage clones which display a peptide of interest can be screened and selected through a binding (to an antibody) test by use of an antibody recognizing GD3, preferably a monoclonal antibody having high specificity to GD3.

By determining DNA sequences of the selected phage clones, a GD3-mimetic peptide of interest can be identified. The DNA sequences can be readily determined through any method known in the art; e.g., a dideoxy method [Proc. Natl. Acad. Sci. USA., 74, 5463-5467 (1977)] or the Maxam-Gilbert method [Method in Enzymology, 65, 499 (1980)]. A commercial sequence kit or similar means may be conveniently employed to determine the corresponding nucleotide sequences.

(Production of the GD3-Mimetic Peptides of the Present Invention)

The GD3-mimetic peptides of the present invention can be produced in accordance with their amino acid sequences through any customary chemical synthesis method, such as a typical liquid-phase or solid-phase peptide synthesis methods.

More specifically, the peptide synthesis methods include a stepwise elongation method in which respective amino acids are successively linked in accordance with amino acid sequence information, to thereby extend the chain; and a fragment condensation method in which fragments are preliminary synthesized from several amino acids and the fragments are coupled. The GD3-mimetic peptides of the present invention can be synthesized through either method.

Any condensation method can be employed for the above peptide synthesis. Examples thereof include an azide method, a mixed acid anhydride method, a DCC method, an active ester method, a redox method, a DPPA (diphenylphosphorylazide) method, a DCC+additive (e.g., 1-hydroxybenzotriazole, N-hydroxysuccinamide, or N-hydroxy-5-norbornene-2,3-dicarboximide) method, and the Woodward method.

The solvent employable in these methods is appropriately selected from customary solvents well-known to be usable in a variety of peptide condensation reactions. Examples include dimethylformamide (DMF), dimethyl sulfoxide (DMSO), hexaphosphoramide, dioxane, tetrahydrofuran (THF), ethyl acetate, and mixtures thereof.

Upon the above peptide synthesis reaction, carboxyl groups of the amino acids and peptides whose groups are not involved in the reaction may be generally protected through esterification to thereby form a lower alkyl ester (e.g., methyl ester, ethyl ester, or tert-butyl ester); or an aralkyl ester (e.g., benzyl ester, p-methoxybenzyl ester, or p-nitrobenzyl ester). A side-chain functional group of an amino acid; e.g., the hydroxyl group of Tyr, may be protected by a group such as acetyl, benzyl, benzyloxycarbonyl, or tert-butyl, but the protection is not essential. The guanidino group of Arg may be protected by an appropriate protective group such as nitro, tosyl, 2-methoxybenzenesulfonyl, methanesulfonyl, benzyloxycarbonyl, isobornyloxycarbonyl, or adamantyloxycarbonyl.

Deprotection reaction of the protective groups of amino acids, peptides, and the finally obtained immunogenic peptides of the present invention having the above protective groups may be performed through any customarily employed method. For example, there may be performed catalytic reduction and chemical deprotection by use of an agent such as liquid ammonia/sodium, hydrogen fluoride, hydrogen bromide, hydrogen chloride, trifluoroacetic acid, acetic acid, formic acid, or methanesulfonic acid.

Purification of the thus-obtained GD3-mimetic peptides of the present invention can be appropriately performed through a routine method such as an ion-exchange resin method, partition chromatography, gel chromatography, affinity chromatography, high-performance liquid chromatography (HPLC), or counter current distribution, which are customarily employed in the field of peptide chemistry.

Alternatively, the GD3-mimetic peptides of the present invention can be produced through a genetic engineering technique employing the DNA sequences according to the present invention encoding the peptides.

The above procedure is carried out through a routine method. For example, synthesis of DNA, production of an expression vector which can express the DNA, and the method of expressing the vector in host cells may be carried out in accordance with generally employed genetic engineering techniques (See Molecular Cloning 2d. Ed., Cold Spring Harbor Lab. Press (1989); Zoku-Seikagaku Jikken Koza "Gene study I, II, and III," edited by The Japanese Biochemical Society (1986); etc.).

The DNA encoding a GD3-mimetic peptide of the present invention may be prepared through a routine method on the basis of the amino acid sequence information of the GD3-mimetic peptide provided by the present invention (e.g., Science, 224, 1431 (1984); and Biochem. Biophys. Res. Comm., 130, 692 (1985); Proc. Natl. Acad. Sci., USA., 80, 5990 (1983)).

More specifically, the DNA can be chemically synthesized through the phosphoramidite method or the triester method. The synthesis can be performed by use of a commercially available automated oligonucleotide synthesizer. Double-strand fragments can be produced from a single-strand product yielded through chemical synthesis including synthesis of complementary strands and annealing of the strands under appropriate conditions; or by addition of complementary strands with an appropriate primer sequence by use of a DNA polymerase.

If desired, the encoding amino acid sequence of the aforementioned DNA may be modified through any known method, such as site-specific variation introduction employing an oligonucleotide (Zoller, M., et al., Nucl. Acids Res., 10, 6487-6500 (1982)), or cassette mutagenesis (Well, J., et al., Gene, 34, 315-323 (1985)).

Production and expression of a peptide of interest by use of the DNA may be carried out through any method known in the art (e.g., Science, 224, 1431 (1984); Biochem. Biophys. Res. Comm., 130, 692 (1985); and Proc. Natl. Acad. Sci. USA., 80, 5990 (1983)). Production and expression of fused peptides and proteins may be performed in accordance with a method of Ohno et al. "Protein Experiment Protocol 1 function analysis, separate vol. of Cell Engineering, Experiment Protocol Series (1997), Shujun-sha) or other methods.

The thus-obtained peptides of interest can be isolated and purified through a variety of separation procedures on the basis of physical, chemical, and other properties (e.g., "Biochemistry Data Book II," 1175-1259, 1st edition, 1st issue, Jun. 23, 1980, Tokyo Kagaku Dojin; Biochemistry, 25 (25), 8274-8277 (1986); and Eur. J. Biochem., 163, 313-321 (1987)). Examples of separation procedures include general reconstruction treatment; treatment by use of a protein-precipitating agent (salting out); centrifugation; osmotic shock procedure; ultrasonic crushing; ultrafiltration; liquid chromatography techniques such as molecular sieve chromatography (gel filtration), adsorption chromatography, ion-exchange chromatography, affinity chromatography, and high-performance liquid chromatography (HPLC); dialysis; and combinations thereof.

The GD3-mimetic peptides of the present invention are more preferably immunogenic peptides having the ability to produce a GD3-specific antibody, which may be an immunogenicity-enhanced form such as a fusion peptide form, peptide fused with a carrier protein, for enhancing immunogenicity, or a multi-antigen peptide form.

The GD3-mimetic peptides of the present invention in fusion form, fused with a carrier protein for enhancing immunogenicity, are obtained by binding any one of the peptides according to the present invention to a customary carrier protein for enhancing imunogenicity.

No particular limitation is imposed on the type of the carrier protein, so long as the protein can enhance immunogenicity, and a variety of proteins and peptides which impart higher immunogenicity on the basis of the carrier effect or which promote immune response of living organisms may be employed as the carrier protein. The carrier protein may be a protein or peptide which additionally exerts a pharmaceutical effect such as anti-tumor activity.

When the GD3-mimetic peptides of the present invention are used as drugs, the carrier protein is selected from pharmaceutically acceptable proteins and peptides. Examples of preferable carrier proteins include keyhole limpet hemocyanin (KLH) and cytokines such as IL-12 and GM-CSF. Examples of the aforementioned proteins and peptides which exert a pharmaceutical effect include IFN-$\alpha$, IFN-$\beta$, IFN-$\gamma$, IL-1, IL-2, TNF, TGF-$\beta$, angiostatin, thrombospondin, and endostatin.

Binding of the above peptide and the carrier protein may be carried out through the aforementioned peptide synthesis method.

The binding may also be carried out by use of the DNA or genes thereof through the aforementioned recombinant technique.

Thus, GD3-mimetic peptides of the present invention in fused form can be obtained.

The GD3-mimetic peptides of the present invention may be multi-antigen peptides (MAP). These peptides are characterized in that a plurality of the GD3-mimetic peptides according to the present invention are displayed on a base molecule.

The MAP form of the GD3-mimetic peptides of the present invention can be preferably produced by use of a dendrimer serving as a base molecule or a skeleton.

As is generally known, a dendrimer is a molecule (e.g., spherical molecule) of a dendritic or star-like configuration, which molecule has branches (repeating units) having a plurality of functional groups (see, e.g., Japanese Kohyo Patent Publication No. 60-500295; Japanese Patent Application Laid-Open (kokai) Nos. 63-99233 and 3-263431; U.S. Pat. Nos. 4,507,466 and 4,568,737; Polymer Journal, 17, p. 117 (1985); Angewandte Chem. Int. Engl., 29, 138-175 (1990); and Macromolecules, 25, p. 3247 (1992)).

No particular limitation is imposed on the dendrimer employed in the present invention, and the dendrimer may be formed of a core serving as a polymerization-initiating site; an internal layer (generation) comprising repeating units connected to the initiation core; and an outer surface formed of functional groups connected to the branches.

Characteristics such as dimensions, morphology, and reactivity of the dendrimer can be regulated by modifying the initiation core, the number of generations, and the type of repeating units employed in each generation. Specifically, the dimensions of a dendrimer can be readily increased by increasing the number of generations to be included (see, e.g., U.S. Pat. No. 4,694,064).

Examples of typical MAP forms of the GD3-mimetic peptides of the present invention include a dendrimer comprising a nitrogen atom serving as an initiation core site; a —$CH_2CH_2CONHCH_2CH_2$— fragment serving as a repeating unit (branch) connecting to each core site; and a plurality of GD3-mimetic peptides connected to the outermost terminals of the dendrimer branches; and a dendrimer comprising an amino acid (e.g., Lys, Arg, Glu, or Asp) serving as an initiation core site, the same amino acid serving as a repeating unit directly connected to each core site, and a plurality of GD3-mimetic peptides connected to terminals of the branches in a similar manner.

The aforementioned dendrimer having a nitrogen atom serving as an initiation core site can be produced through a customary method or obtained as a commercial product (Polysciences, Inc., 400 Vally Road, Warrington, Pa., 18976 U.S.A.). The aforementioned dendrimer having an amino acid serving as an initiation core site and the same amino acid serving as a repeating unit directly connected to each initiation core site can be produced through the aforementioned peptide synthesis method. In addition, commercial products such as $Fmoc_8$-$Lys_4$-$Lys_2$-Lys-$\beta$Ala-Alko resin (SEQ ID NO:11) (product of Watanabe Kagaku Kogyo) may also be used.

More specifically, the aforementioned dendrimers can be produced through condensation of $\alpha,\omega$-diamino acids serving as repeating units and a resin for synthesizing a solid-phase peptide, where two amino groups of each amino acid have been protected by protective groups, which are identical to or different from each other, in the presence or absence of a spacer; and repetition of removal of the protective groups.

Resins typically employed for peptide synthesis can be employed as the resin for synthesizing a solid-phase peptide. Examples include polystyrene resin, polyacrylamide resin, polystyrene-polyethylene glycol resin, the terminal groups of these resins being capped with a functional group such as chloromethyl, 4-(hydroxymethyl)phenoxy, or 4-(($\alpha$-2', 4'-dimethoxyphenyl)-9-fluorenylmethoxycarbonylaminomethyl)phenoxy. One or more amino acids may be employed as spacers.

Examples of $\alpha,\omega$-diamino acids include lysine, ornithine, 1,4-diaminobutyric acid, and 1,3-diaminopropionic acid. Removal of the protective groups can be performed through the aforementioned peptide synthesis method. Examples of functional groups include an amino group, a carboxyl group, and a hydroxyl group.

The number of branch layers is adjusted to 2n by performing condensation of a repeating unit and removal of protective groups n times in total. Specifically, the number may fall within a range of 2 to 16.

By binding the GD3-mimetic peptides according to the present invention to the functional groups connected to terminals of the branches of the dendrimer, an MAP of interest can be obtained. The procedure can be performed in accordance with the aforementioned peptide synthesis method.

The thus-produced MAP can be purified through chromatography or a similar method in a routine manner by use of a resin which attains size exclusion in a matrix such as Sephacryl S-300 (product of Pharmacia).

The GD3-mimetic peptides according to the present invention which are caused to be bound to the terminal of branches of the MAP according to the present invention are not necessarily identical with one another, and different species may be combined arbitrarily. Examples of combinations of different GD3-mimetic peptides include a combination of SEQ ID NOS: 1, 3, and 4; and a combination of a peptide having an amino acid sequence of 15 amino acid residues shown in any one of SEQ ID NOS: 1 to 4 and a peptide having an amino acid sequence of nine amino acid residues shown in FIG. 2. Such a complex MAP enhances stability thereof in the blood and tissues of the target to which the MAP is administered, and enhances immunogenicity or other properties of the molecule to which the MAP has been bound. Thus, production of a GD3 antibody by any of the GD3-mimetic peptides of the present invention may be promoted.

Any of the MAPs of the present invention may be transformed into a complex MAP in which the aforementioned carrier protein (e.g. polypeptide promoting immune response such as IL-12 or GM-CSF) for enhancing immunogenicity is bound as a portion of the GD3-mimetic peptide of the present invention or to an initiation core site. Other gangliosides which are expressed on tumor cells other than the GD3-mimetic peptides of the present invention, such as one or more mimetic peptides (e.g., GM2, GM3, GD1, GD2, GD3, and GT3), can also be employed as MAP constituents in combination with any of the GD3-mimetic peptides of the present invention. Examples of complex MAPs include a combination of at least one peptide containing an amino acid sequence represented by any one of SEQ ID NOS: 1 to 4 or an amino acid sequence shown in FIG. 2 with a replica peptide mimicking GD1α (disclosed in the aforementioned Japanese Patent Application Laid-Open (kokai) No. 10-237099.

The thus-produced MAP forms of the GD3-mimetic peptides of the present invention exhibit excellent immunogenicity and, therefore, can exert desired effects; i.e., inducing production of an anti-GD3 antibody or increasing production of the antibody.

The GD3-mimetic peptides of the present invention in MAP form exert effects as desired for a vaccine; i.e., a carcinostatic effect and an inhibitory effect for cancerous metastasis. In addition, an arbitrary drug such as a drug promoting immune response is incorporated into the MAPs and the thus-modified MAPs can be administered. Thus, MAPs are advantageous in that induction of a target antibody can be promoted, production of an antibody can be further increased, and other effects can be enhanced.

(Pharmaceutical Composition of the Present Invention)

The present invention provides a pharmaceutical composition for human and animals containing, as an active ingredient, any of the GD3-mimetic peptides of the present invention.

The pharmaceutical composition is useful as, among others, a cancer-diagnostic agent on the basis of the effect that the active ingredient binds to an antibody to a cancer-related GD3 antigen.

Preferably, the pharmaceutical composition of the present invention contains, as an active ingredient, any of the GD3-mimetic peptides of the present invention in the form of an immunogenic peptide having the ability to produce a GD3-specific antibody.

The GD3-mimetic peptides of the present invention in the form of the above immunogenic peptide mimic the structure of GD3 and exhibit an immunogenicity similar to that of GD3. Thus, the peptides exhibit anti-tumor effect on the basis of activation of cytoxic effects depending on a complement or an induced or produced antibody or activation of cytoxic T cells; and an intercellular adhesion inhibitory effect by mediation of GD3 in tumor cells expressing GD3. The peptides are useful for a variety of pharmaceutical uses.

Examples of use of the drugs provided by the pharmaceutical composition include a vaccine for stimulating induction of an antibody recognizing GD3 or enhancing production of the antibody; anti-tumor use, carcinostatic use, or inhibitory use for cancerous metastasis; and treatment for GD3-expressing tumors or cancer, particularly diseases selected from the group consisting of melanoma, cancer of large intestine, ovarian cancer, liver cancer, breast cancer, brain cancer, kidney cancer, pancreas cancer, cervical cancer, esophageal cancer, lung cancer, and stomach cancer.

The pharmaceutical composition of the present invention can be prepared as a composition containing an pharmaceutically effective amount of any of the GD3-mimetic peptides of the present invention and a pharmaceutically acceptable carrier.

The pharmaceutically acceptable carriers employed in the present invention are known in the art and are appropriately selected in accordance with the form of the composition to be prepared. When the composition to be prepared is an aqueous solution, carriers such as water and physiological buffers can be used without limitation, and glycol, glycerol, and injectable organic esters such as olive oil may also be used.

The pharmaceutical composition of the present invention may further contain another active ingredient and an arbitrary ingredient for stabilizing absorption of the active ingredient and enhancing absorption. Examples of arbitrary ingredients include hydrocarbons such as glucose, sucrose, and dextran; antioxidants such as ascorbic acid and glutathione; chelating agents; stabilizers such as low-molecular-weight proteins and albumin; and vehicles.

Into the pharmaceutical composition of the present invention, arbitrary additives for designing drug preparations can be appropriately incorporated. Examples include a variety of generally employed additives such as antiseptic agents, tonicity agents, buffers, stabilizers, solubilizers, and absorption promoters. Examples of the antiseptic agents include those effective for fungi and bacteria such as benzalkonium chloride, benzethonium chloride, chlorhexidine, parabens (e.g., methyl parben, ethyl paraben), and thimerosal. Examples of tonicity agents include polyhydric alcohols such as D-mannitol, D-sorbitol, D-xylitol, glycerin, glucose, maltose, sucrose, and propylene glycol; and electrolytes such as sodium chloride. Examples of stabilizers include tocopherol, butylhydroxyanisole, butylhydroxytoluene, ethylenediaminetetraacetic acid salts (EDTA), and cysteine.

One form of the pharmaceutical composition of the present invention is a liposome preparation. This preparation will next be described in detail. The preparation can be produced by causing any of the GD3-mimetic peptides of the present invention to be held on liposome comprising, as a membrane-forming ingredient, acidic phospholipid or comprising, as membrane-forming ingredients, neutral phospholipid and acidic phospholipid.

No particular limitation is imposed on the type of neutral phospholipid and acidic phospholipid serving as membrane-forming ingredients, and lipid species which are customarily used in such liposome preparations may be used singly or in combination of two or more species.

Membrane of the liposome is formed through a customary method by use of acidic phospholipid as a membrane-forming ingredient or by use of neutral phospholipid and acidic phospholipid in combination as membrane-forming ingredients. The acidic phospholipid content is about 0.1 to about 100 mol % based on the total amount of liposome membrane-forming ingredients, preferably about 1 to about 90 mol %, more preferably about 10 to about 50 mol %.

Upon preparation of the liposome membrane, additives such as cholesterol may be incorporated into phospholipid, to thereby control flowability, thus facilitating preparation of liposome membrane. The amount of cholesterol incorporated into phospholipid is generally equivalent to that of phospholipid or less, preferably 0.5-1 equivalent.

The proportion of acidic phospholipid to active ingredient(s) contained in a liposome dispersion is about 0.5 to about 100 equivalents, preferably about 1 to about 60 equivalents, more preferably about 1.5 to about 20 equivalents. The amount of any of the GD3-mimetic peptides of the present invention is some mol % to some tens of mol % based on the total lipid species, preferably about 5 to about 10 mol %, with about 5 mol % being typically employed.

Preparation, concentration, particle size control, and other processes of the liposome can be performed through a customary method. The aforementioned various additives may be incorporated into the liposome preparation in accordance with needs.

Upon production of liposome, fatty acid (e.g., behenic acid, stearic acid, palmitic acid, myristic acid, or oleic acid), an alkyl group, a cholesteryl group, or a similar group may be bound to any of the GD3-mimetic peptides of the present invention. Production of a liposome preparation by use of such a modified peptide can be performed through a customary method (e.g., Long Circulating Liposomes: Old drugs, New therapeutics., M. C. Woodle, G. Storm, Eds: Springer-Verlag Berlin (1998)).

No particular limitation is imposed on the amount of active ingredient(s) contained in the pharmaceutical composition (drug preparation) of the present invention, and the amount can be selected from a wide range, so long as it is pharmaceutically effective.

Generally, any of the GD3-mimetic peptides of the present invention is contained in a drug preparation in an amount of about 0.00001 to about 70 wt. %, preferably about 0.0001 to about 5 wt. %. No particular limitation is imposed on the amount of administration of the drug preparation, and the amount is appropriately selected from a wide range in accordance with desired therapeutic effects, the method (way) of administration, the therapy period, and the age, sex, and other conditions of patients. Generally, the daily dose per patient per body weight (kg) preferably falls within a range of about 0.01 µg to about 10 mg as reduced to active ingredient(s), preferably about 0.1 µg to about 1 mg. The drug preparation may be administered once per day or in a divided manner.

The pharmaceutical composition of the present invention is preferably employed as the aforementioned vaccine composition. In use as a vaccine composition, the composition of the present invention is preferably administered along with a pharmaceutically effective amount of an adjuvant in combination so as to enhance its anti-tumor effect.

No particular limitation is imposed on the type of the adjuvant, and examples include Freund's complete adjuvant, muramyl dipeptide, BCG, IL-12, N-acetylmuramin-L-alanyl-D-isoglutamine (MDP), thymosin α1, and QS-21. Although the amount of adjuvant to be administered is limited depending on a type of pathological conditions of human and animals caused, after administration, by immune reaction such as malacia, pain, and erythema of the skin; fever; headache; or muscle pains, the daily dose of adjuvant per patient per body weight (kg) is generally about 0.1 µg to about 1,000 µg, preferably about 1 µg to some hundreds of µg.

The pharmaceutical composition of the present invention can be used in combination with other drugs, such as an immune-response-promoting pepetide and a cancer chemotherapy agent (anti-cancer agent). The amount of the drug administered in combination is appropriately determined in accordance with the pharmaceutically effective amount of the drug. For example, when GM-CSF is used, the daily dose thereof per body weight (kg) of the patient is generally about 0.1 µg to about 1,000 µg, preferably about 1 µg to some hundreds of µg.

Examples of the aforementioned drugs used in combination include cancer chemotherapy agents including 5-fluorouracil (5-FU), such as alkylating agents, metabolism antagonists, anti-tumor antibiotic preparations, anti-tumor vegetable-originating preparations; and the aforementioned cytokines having an anti-tumor activity.

Upon combination use, a drug can be incorporated into MAP form GD3-mimetic peptides of the present invention in the aforementioned manner. In addition, a drug delivery substance such as a microdevice having a microchamber which can accommodate other drugs and which accommodates the GD3-mimetic peptides of the present invention can also be used. Examples of such drug delivery substances include biological substances such as liposome, microcapsules having permeable or semi-permeable membranes, and other microdevices having microchambers. These substances are non-toxic and may be biodegradable.

Binding of these drug delivery substances and the GD3-mimetic peptide of the present invention can be preformed through a customary method (e.g., Harlow and Lane, Antibodies: A laboratory manual, Cold Spring Harbor Lab. Press (1988); and Hermanson, Bioconjugate Techniques, Academic Press (1996)). A pharmaceutical composition containing a substance such as a cytokine containing a carcinostatic and exerting anti-tumor activity is produced through a known method (e.g., Liposomal application to cancer therapy, Y. Namba, N. Oku, J., Bioact. Compat. Polymers, 8, 158-177 (1993)).

When the pharmaceutical composition of the present invention is employed as a diagnostic agent, any of the GD3-mimetic peptides of the present invention—the active ingredient—may be labeled for its detection. Labeling can be performed through a customary method, and materials such as radioactive compounds, fluorescent substances, enzymes, biotin, and contrast media can be used.

Through employment of such a diagnostic agent, an anti-GD3 antibody contained in a variety of samples such as cancer tissues and cells and body fluids such as blood can be detected. Thus, the diagnostic agent is useful for cancer diagnosis, monitoring of pathological conditions, etc.

(DNA of the Present Invention)

The present invention provides DNA comprising a sequence encoding any of the GD3-mimetic peptides of the present invention. The DNA is useful in the aforementioned production of the GD3-mimetic peptides of the present invention through a genetic engineering technique. The DNA is suitably used for producing a DNA vaccine containing the DNA as an active ingredient.

As mentioned above, the DNA encoding the GD3-mimetic peptides of the present invention is preferably DNA encoding immunogenic peptides having the ability to produce a GD3-specific antibody which immunogenic peptides are embodiments of the GD3-mimetic peptides of the present invention. Furthermore, the DNA may encode the aforementioned particularly preferred forms of the GD3-mimetic peptides of the present invention.

The aforementioned vaccine comprises a pharmaceutical composition containing, as an active ingredient, the DNA encoding immunogenic peptides having the ability to produce a GD3-specific antibody which immunogenic peptides are embodiments of the GD3-mimetic peptides of the present invention or a recombinant expression vector which can express the DNA.

The pharmaceutical composition is useful for a DNA vaccine targeting cancer cells or tissues of mammals including human, and uses of the pharmaceutical composition are similar to those described in relation to the pharmaceutical composition containing, as an active ingredient, any of the GD3-mimetic peptides of the present invention.

The aforementioned DNA vaccine can be prepared as a pharmaceutical composition though a customary method by use of a pharmaceutically acceptable carrier. Preferably, the vaccine contains a physiologically acceptable solution such as sterilized physiological saline or sterilized buffered physiological saline. Similar to the case of the aforementioned pharmaceutical composition containing, as an active ingredient, any of the GD3-mimetic peptides of the present invention, the composition may be a liposome drug preparation and may be used in combination with an adjuvant or a similar material.

The pharmaceutical composition may contain an arbitrary drug and additives. Examples of the drug include a drug such as calcium ions promoting incorporation of DNA into cells, and examples of the additives include materials for facilitating transfection, such as the aforementioned liposome, fluorocarbon emulsions, cochleates, tubules, gold particles, biodegradable microspheres, and cationic polymers.

The amount of DNA which can be expressed and is introduced to a vaccination host or the amount of transcripted RNA which is introduced to a vaccination host is selected from a wide range of amount of administration. The amount is varied in accordance with, for example, the capacity of employed transcription and translation promoters. The intensity of immune response varies in accordance with the level of expression of protein and the immunogenicity of expressed gene products. Generally, the vaccine is parenterally administered in an effective amount of about 1 ng to about 5 mg based on DNA, preferably about 100 ng to about 2.5 mg, more preferably about 1 μg to about 750 μg, still more preferably about 10 μg to 300 μg. Generally, the vaccine is administered directly to muscle tissues. Alternatively, there may be also employed other administration methods such as hypodermic injection, introduction to the corium, skin impression, intraperitoneal administration, intravenous administration, and inhalation.

In general, the vaccine is administered not once, but booster vaccination is effected one or more times so as to enhance the effect of the vaccine while conditions of the administered specimens are monitored. Alternatively, vaccination of DNA may be followed by booster by use of the aforementioned pharmaceutical composition comprising the GD3-mimetic peptide of the present invention. In addition, the aforementioned various combinations may enhance the therapy efficacy.

No particular limitation is imposed on the type of recombinant expression vector which can express the DNA of the aforementioned DNA vaccine, and expression vectors generally employed in such types of DNA vaccines and other employable expression vectors can be used. These vectors can be produced through a customary method.

(Antibody of the Present Invention)

The GD3-mimetic peptides of the present invention function as antigens and produce the corresponding antibodies. Specifically, any of the peptides which binds to GD3 binds to cells such as malignant tumor cells (e.g., melanoma cells) which express GD3, thereby producing an antibody (neutralizing antibody) which inhibits proliferation of the cells and exhibits activity to inhibit metastasis of the cells. The present invention also provides such an antibody.

Confirmation of production of such an antibody is regarded as a test for diagnosing that the GD3-mimetic peptide of the present invention is an immunogenic peptide having the ability to produce a GD3-specific antibody.

The antibodies according to the present invention include monoclonal and polyclonal antibodies. These antibodies can be produced through a customarily employed technique by use of the GD3-mimetic peptide as an immunogen.

Next, production of the monoclonal antibody will be described in detail. The monoclonal antibody can be produced, for example, by fusing plasma cells (immunocytes) of a mammal which has been immunized with the above immunogen and plasmacytoma cells (myeloma cells) of the mammal, to thereby produce fused cells (hybridomas); selecting a clone producing a desired antibody recognizing GD3 (monoclonal antibody); and culturing the clone. The monoclonal antibody is fundamentally produced in accordance with a routine method (e.g., Hanfland, P., Chem. Phys. Lipids, 15, 105 (1975); Hanfland, P., Chem. Phys. Lipids, 10, 201 (1976); and Koscielak, J., Eur. J. Biochem., 37, 214 (1978)).

No particular limitation is imposed on the mammal which is immunized with the immunogen in the above method, and mice, rats, etc. are preferably used from the viewpoint of compatibility to plasmacytoma cells to be fused. Immunization can be performed through a customary method such as administration of the above immunogen to a mammal through injection (e.g., intravenous, intradermal, hypodermal, or intraperitoneal).

More specifically, when mice are used, preferably, the immunogen is diluted to an appropriate concentration with a diluent such as physiological phosphate buffered saline (PBS) or physiological saline and is administered, in combination with an optional customary adjuvant in accordance with needs, to an animal specimen several times at intervals of 2 to 14 days in a total amount of about 100 to about 500 μg/mouse. Examples of the adjuvant which is preferably employed in the above process include a pertussis vaccine, Freund's complete adjuvant, and ALUM. Preferably employed immunocytes include spleen cells which have been extirpated about three days after final administration of the immunogen.

A variety of known mammal plasmacytoma cells can be employed as counter parent cells to be fused with the above immunocytes. The fusion can be performed through any known method, such as the method described in Milstein et al. (Method in Enzymology, 73, 3 (1981)). Isolation and cloning of the yielded hybridomas can be performed through customary methods.

The target antibody-producing strains can be retrieved through a variety of methods generally employed for detecting antibodies ("Hybridoma Method and Monoclonal Antibody," issued by R&D Planning, 30-53, Mar. 5, 1982). Examples of the methods include the ELISA method (Engvall, E., Meth. Enzymol., 70, 419-439 (1980)), a plaque method, a spot method, an agglutination method, an ochterlony method, and radioimmunoassay (RIA). Upon retrieval, the aforementioned immunogen and GD3 can be employed.

The thus-yielded hybridomas producing a desired monoclonal antibody recognizing GD3 can be subcultured in a customary medium and preserved for a long period of time in liquid nitrogen. Examples of methods for collecting a monoclonal antibody from the hybridomas include a method comprising culturing the hybridomas in a routine manner and collecting an antibody from a culture supernatant; and a method comprising administering the hydridomas to a mammal compatible with the hybridomas for proliferating the hybridomas and collecting an antibody from the ascites. The former method is suitable for producing a high-purity antibody, whereas the latter method is suitable for mass production of an antibody.

The culture supernatant and mouse's ascites obtained through the above methods and containing antibody-producing hybridomas may be employed as crude antibody liquids. Alternatively, the crude liquids may be purified through a routine method; i.e., method such as ammonium sulfate fractionation, salting out, gel filtration, ion-exchange chromatography, or affinity chromatography such as protein A column chromatography, to thereby yield a purified antibody.

EXAMPLES

The present invention will next be described in more detail by way of examples, which should not be construed as limiting the invention thereto.

The following abbreviations are employed herein.
TBS: Tris phosphate-buffered saline
TC: tetracycline
KM: kanamycin
PEG/NaCl: polyethylene glycol/sodium chloride
TFA: trifluoroacetic acid Example 1

Identification of GD3-mimetic Peptide (1) Preparation of Phage Display Libraries According to the procedure disclosed by Nishi T., Saya H., et al. (FEBS Letter, 399, 237-240 (1996)), random DNA fragments encoding peptides of random 15 amino acid residues were inserted into phage coat protein pIII gene, to thereby prepare phage display libraries of interest containing genes capable of expressing peptides of random 15 amino acid residues on the coat surface of respective phages.

Since the phages contain a TC resistant gene, E. coli infected with the phages is TC resistant. The phage libraries thus constructed were stored in a TBS solution containing 0.02% NaN$_3$.

Characteristic features of the above-mentioned phage display libraries are described by Scott, J. K. and Smith G. P. (Science, 249, 386-390 (1990)).

(2) Immobilization of Anti-GD3 Monoclonal Antibody

The anti-GD3 antibody employed is an anti-GD3 monoclonal antibody 4F6 (hereinafter referred to as GD3 antibody 4F6). The GD3 antibody 4F6 is a mouse monoclonal antibody (IgG) against GD3 (Thomas C. P., et al., Glycoconj. J., 13 (3), 377-384 (1996)), which was kindly provided by Dr. Jacques Portoukalian (INSERM, France).

A recombinant protein A Sepharose suspension (50 µL) (rProtein A Sepharose Fast Flow; product of Pharmacia Biotech K.K., Code No: 17-1279-01, Lot No: 237393) was transferred to a 0.5-mL Eppendorf tube, and TBS (400 µL) was added thereto. Subsequently, GD3 antibody 4F6 (1 mL) was added, and the mixture was allowed to react overnight at 4° C. under thorough stirring. After completion of reaction, the mixture was centrifuged at 3,000 rpm for 5 minutes, the supernatant was discarded, TBS (0.5 mL) was added to the residue, and the mixture was thoroughly stirred. The resultant mixture was transferred to a 1.5-mL Eppendorf tube. TBS (0.5 mL) was added thereto, the mixture was centrifuged at 3,000 rpm for 5 minutes, and the supernatant was discarded. Subsequently, TBS (1 mL) was added to the residue, the mixture was centrifuged at 3,000 rpm for 5 minutes, and the supernatant was removed. TBS (100 µL) was added to the residue, to thereby yield a suspension; i.e., a suspension of recombinant protein A Sepharose (100 µL) bound to GD3 antibody 4F6, which was stored at 4° C. until use.

An aliquot of the thus-obtained recombinant protein A Sepharose suspension (50 µL) was transferred to a 1.5-mL Eppendorf tube, and TBS (900 µL) was added thereto. Subsequently, 12 mg/mL mouse immunoglobulin standard serum (Code No: RS10-101-2; product of Bethyl; purchased from Cosmo Bio Co., Ltd.) in TBS (total volume of the resultant solution: 100 µL) was added, and the mixture was allowed to react overnight at 4° C. under thorough stirring. (Protein A was reacted with an excessive amount of IgG so as to minimize the amount of protein A remaining unreacted.) After completion of reaction, the mixture was centrifuged at 3,000 rpm for 5 minutes, the supernatant was removed, TBS (1 mL) was added to the residue, and the mixture was thoroughly stirred. The resultant mixture was transferred to a 1.5-mL Eppendorf tube. The mixture was centrifuged at 3,000 rpm for 5 minutes, and the supernatant was removed. After this procedure was repeated three times, TBS (100 µL) was added to the residue, to thereby prepare a suspension; i.e., a suspension of a recombinant protein A Sepharose (100 µL) bound to mouse IgG (250 µg), which was stored at 4° C. until use.

(3) Preparation of E. coli

E. coli employed as a host of phage is E. coli K91KAN (kanamycin resistant strain; kindly provided by Professor SAYA, Hideyuki, Department of Tumor Genetics and Biology of Kumammoto University).

By use of a disposable platinum loop, E. coli K91KAN was inoculated into an NZY plate containing 100 µg/mL kanamycin (product of Wako Pure Chemicals Industries, Ltd.) for incubation at 37° C. overnight. On the following day, the plate was removed from the incubator and stored at 4° C. until use.

The day before the E. coli was infected with phages, a small amount of the E. coli which had been stored at 4° C. in the plate was collected by use of a platinum loop, and inoculated into an NZY medium (5 mL) containing 100

μg/mL kanamycin, followed by shaking culture at 200 rpm at 37° C. overnight (pre-culture). On the following day, the cultured mixture (100 μL) was transferred to a fresh NZY medium (10 mL), followed by shaking culture at 37° C. for 4 hours. Thereafter, in order for the cells to develop F-cilia, shaking was stopped, and the cells were left to stand for 30 minutes. The thus-prepared E. coli cells were infected with phages as described below.

The aforementioned NZY medium was obtained through the following steps: NZ amine A (product of Wako Pure Chemicals Industries, Ltd.; Code No: 541-00241) (10 g), brewer's yeast extraction (trade name: EBIOS, product of Asahi Breweries, Ltd.) (5 g), and NaCl (5 g) were dissolved in distilled water (1 L); 5N NaOH (1 mL) was added thereto; pH of the mixture was adjusted to 7.5; the mixture was sterilized in an autoclave; and the resultant mixture was stored at room temperature until use.

(4) Amplification of Phage

The E. coli host cells were infected with the phages prepared in the procedure described in (1).

Briefly, the above-prepared E. coli K91KAN (10 μL) and a diluted phage preparation (10 μL) were placed in a 15-mL centrifuge tube, and the mixture was allowed to react at room temperature for 15 minutes. An NZY medium (containing 0.2 μg/mL TC) (1 mL) which had been heated in advance to 37° C. was added to the mixture, followed by shaking culture at 2,000 rpm at 37° C. for 40 minutes. An aliquot (200 μL) of the resultant mixture was inoculated into an NZY plate (containing 20 μg/mL TC and 100 μg/mL KM) for incubation at 37° C. overnight. On the following day, the number of colonies was counted.

A negative control was prepared by adding E. coli K91KAN (10 μL) to the dilution liquid (10 μL). Since this mixture remained sensitive to TC, amplification of phages did not occur in the TC-containing NZY plate.

Amplification of phages that were recovered through biopanning, which will be described herein later, was performed in the following manner.

The entire amount of the phage solution, excepting the amount (2 μL) to be used for titer measurement, was placed in a 1.5-mL Eppendorf tube, and the above-prepared E. coli K91KAN (100 μL) was added thereto, followed by reaction at room temperature for 15 minutes. After completion of reaction, the entire amount of the mixture was added to a TC-supplemented NZY medium (20 mL; the amount of TC: 0.2 μg/mL) which had been heated in advance to 37° C. in a 50-mL centrifuge tube, followed by shaking culture at 200 rpm at 37° C. for 40 minutes. 20 mg/mL TC (20 μL) was added, and the mixture was again subjected to shaking culture at 37° C. overnight. On the following day, the resultant mixture was centrifuged at 3,000 rpm for 10 minutes. The supernatant was transferred to an Oakridge centrifuge tube and centrifuged at 12,000 rpm for 10 minutes, to thereby remove E. coli cells completely. The supernatant was transferred to another Oakridge centrifuge tube, and PEG/NaCl (3 mL) was added thereto, followed by thorough stirring. The resultant mixture was left to stand at 4° C. for 4 hours or more.

Subsequently, centrifugation was performed at 12,000 rpm for 10 minutes for causing sedimentation of amplified phages. The supernatant was removed, and the phage sediment was suspended in TBS (1 mL). The suspension was transferred to a 1.5-mL Eppendorf tube and centrifuged at 15,000 rpm for 10 minutes, to thereby remove insoluble substances. The supernatant was transferred to another Eppendorf tube, PEG/NaCl (150 μL) was added thereto, and the mixture was thoroughly stirred and left to stand at 4° C. for 1 hour or more.

The mixture was centrifuged at 15,000 rpm for 10 minutes, to thereby allow the phages to precipitate. The supernatant was removed, and the precipitated phage pellet was resuspended in TBS (200 μL) containing 0.02% $NaN_3$. The suspension was centrifuged at 15,000 rpm for 10 minutes, to thereby settle insoluble substances. The sediment was transferred to a 500-μL Eppendorf tube for storage at 4° C., and employed as the source of "amplified phage" in each round of panning.

The phages were titered in the following manner.

For titration of phages recovered in each round, $10^2$-, $10^3$-, and $10^4$-fold diluted phage preparations were used, whereas for titration of amplified phages, $10^7$-, $10^8$-, and $10^9$-fold diluted preparations were used. TBS/gelatin (product of Wako Pure Chemicals Industries, Ltd.) was employed as a dilution solution, and dilution was performed in accordance with the following dilution scheme.

×$10^2$ dilution: phage solution (2 μL)+TBS/gelatin (198 μL)
×$10^3$ dilution: $10^2$-fold diluted phage solution (10 μL)+TBS/gelatin (90 μL)
×$10^4$ dilution: $10^2$-fold diluted phage solution (2 μL)+TBS/gelatin (198 μL)
×$10^6$ dilution: $10^4$-fold diluted phage solution (2 μL)+TBS/gelatin (198 μL)
×$10^7$ dilution: $10^6$-fold diluted phage solution (10 μL)+TBS/gelatin (90 μL)
×$10^8$ dilution: $10^6$-fold diluted phage solution (2 μL)+TBS/gelatin (198 μL)
×$10^9$ dilution: $10^8$-fold diluted phage solution (10 μL)+TBS/gelatin (90 μL)

The phage titer was calculated from the following equation.

$$\text{Titer/mL} = \text{colony} \times 1{,}020\ (\mu L)/200\ (\mu L) \times 1{,}000\ (\mu L)/10\ (\mu L) \times \text{dilution factor}$$

The total titer of the recovered phages was calculated by multiplying the above value by the entire volume (mL) of the recovered phage solution.

Since the phages employed for reaction have a titer of $6.2 \times 10^{10}$, recovery rate (%) is defined as "total titer of recovered phages/$6.2 \times 10^{10}$"×100.

(5) Screening (Biopanning) for Phage Clones which are Bound to Anti-GD3 Antibody In screening (biopanning) for phage clones expressing peptides capable of binding to GD3 antibody 4F6 with specificity, for the purpose of efficient screening for phages capable of binding to the Fab region of GD3 antibody 4F6, GD3 antibody 4F6 was reacted with the phage library from which phages that bind themselves to standard mouse IgG and/or recombinant protein A Sepharose had been excluded in advance.

Specifically, biopanning was performed through the following procedure.

Round 1:

Standard mouse IgG—recombinant protein A Sepharose (10 μL) and recombinant A Sepharose (50 μL) were dissolved in PBS (340 μL), and a phage library (10 μL) ($6.2 \times 10^{10}$ titer) was added thereto. The mixture was allowed to react in a 500-μL Eppendorf tube at 4° C. overnight, followed by centrifugation at 30,000 rpm for 3 minutes, to thereby remove phage particles bound to standard mouse IgG and/or recombinant protein A Sepharose.

The supernatant (380 μL) and the GD3 antibody 4F6-recombinant protein A Sepharose (50 μL) prepared in step (2) above were transferred to a 500-μL Eppendorf tube and allowed to react at 4° C. for 5 hours, followed by centrifugation at 3,000 rpm for 3 minutes.

The supernatant was discarded, and PBS (0.5 mL) was added to the sediment, to thereby prepare a suspension. The suspension was then transferred to a 1.5-mL Eppendorf tube, followed by centrifugation at 3,000 rpm for 3 minutes. After this procedure was repeated twice, the supernatant was discarded, and PBS (500 μL) was added to the sediment, whereby a suspension was obtained. The suspension was transferred to a 500-μL Eppendorf tube, followed by centrifugation at 3,000 rpm for 3 minutes. The supernatant was discarded, an extraction buffer (50 μL) was added to the sediment, and the mixture was left to stand at room temperature for 15 minutes under gentle stirring performed every 3 minutes, followed by centrifugation at 3,000 rpm for 3 minutes. The supernatant was transferred to a concentrator (Centricon™ 30 Concentrator: product of Amicon Corporation) and neutralized with 1M Tris (pH 9.1) (75 μL), and then TBS (2 mL) was added thereto.

The mixture was centrifuged at 5,000 rpm for 20 minutes, TBS (2 mL) was added, and centrifugation was performed at 5,000 rpm for 20 minutes.

The phage solution remaining on the filter of the Centricon was transferred to a 1.5-mL Eppendorf tube. The filter was washed with TBS (50 μL), and the washings were added to the Eppendorf tube (total volume: 470 μL). The obtained phages were amplified (4).

Round 2:

The amplified phages (100 μL) prepared in Round 1 and standard mouse IgG—recombinant protein A Sepharose (10 μL; 25 μg) were dissolved in PBS (350 μL), and the mixture was transferred to a 500-μL Eppendorf tube for reaction at 4° C. overnight. Subsequently, recombinant protein A Sepharose (50 μL) was added, and the mixture was allowed to react at 4° C. overnight and then centrifuged at 3,000 rpm for 3 minutes, yielding a supernatant (500 μL).

The supernatant (500 μL) was transferred to a 1.5-mL Eppendorf tube, an anti-GD3 antibody solution (1 mL) was added thereto, and the mixture was allowed to react at 4° C. overnight, followed by centrifugal separation at 3,000 rpm for 3 minutes.

Subsequently, recombinant protein A Sepharose (50 μL) was added thereto, and the mixture was allowed to react at 4° C. for 3 hours, then centrifuged at 3,000 rpm for 3 minutes. The supernatant was discarded, and TBS (1 mL) was added to the sediment, to thereby prepare a suspension. The suspension was transferred to a 1.5-mL Eppendorf tube and then centrifuged at 3,000 rpm for 3 minutes. After this procedure was repeated twice, the supernatant was discarded, an extraction buffer (50 μL) was added to the sediment, and the mixture was left to stand at room temperature for 15 minutes under gentle stirring performed every 3 minutes, followed by centrifugation at 3,000 rpm for 3 minutes. The supernatent was transferred to a concentrator and neutralized with 1M Tris (pH 9.1) (75 μL), and then TBS (2 mL) was added thereto. The mixture was centrifuged at 5,000 rpm for 20 minutes, TBS (2 mL) was added, and centrifugation was performed at 5,000 rpm for 20 minutes. The phage solution remaining on the filter of the Centricon was transferred to a 1.5-mL Eppendorf tube. The filter was washed with TBS (50 μL), and the washings were added to the Eppendorf tube (total volume: 230 μL). The obtained phages were amplified.

Round 3:

The general procedure employed in Round 1 was repeated by use of the amplified phages (100 μL) prepared in Round 2. Thus, through reaction of phages with an anti-GD3 antibody solution, amplified phages were obtained. The thus-obtained phages were centrifuged by use of Centricon, whereby eluate was recovered in a total amount of 110 μL.

The results of the above 3 rounds of panning (phage clone recovery rates of the respective rounds) are shown in Table 1.

TABLE 1

| Titer/well | fd wild type | GD3R-1 | GD3R-2 | GD3R-3 | GD3R-4 |
|---|---|---|---|---|---|
| $10^9$ | 0.024 | 0.017 | 0.055 | 0.05 | 0.109 |
| $10^9$ | 0.08 | 0.026 | 0.034 | 0.086 | 0.116 |
| $10^{10}$ | 0.045 | 0.067 | 0.128 | 0.058 | 0.14 |
| $10^{10}$ | 0.044 | 0.055 | 0.109 | 0.017 | 0.102 |
| $10^{11}$ | 0.03 | 0.094 | 0.049 | 0.094 | 0.386 |
| $10^{11}$ | 0.029 | 0.086 | 0.012 | 0.108 | 0.315 |

In Table 1, "fd wild type" refers to the wild phage strain of prototype—no peptide being inserted—which was provided to construct phage libraries in Example 1. The prototype phages were prepared through the following process and employed in the present test. Briefly, phage vectors formed of DNA molecules of the phages that constitute the phage peptide library were cleaved for removal of peptide insertion sites, and the remaining vector fragments were ligated. The thus-reconstructed vectors were used to transform *E. coli* JM109 (purchased from Takara), the resultant transformants were cultured with an NZY medium overnight, and the amplified phages were recovered.

Sequencing of the peptides expressed by the phage clones prepared through the 3 rounds of panning described above was performed as follows.

From each of the plates obtained through the above-described titer measurement performed after completion of 3 rounds of biopanning, arbitrary 32 colonies were randomly picked up, inoculated into a new NZY plate, and incubated at 37° C. overnight. The resultant plate, which served as a master plate, was stored at 4° C.

In an NZY medium (20 mL, containing 20 μg/ml TC) placed in a 50-mL centrifuge tube, each colony of the master plate was suspended, followed by shaking culture at 200 rpm at 37° C. overnight.

The culture was subjected to centrifugal separation at 3,000 rpm for 10 minutes. The supernatant was transferred to an Oakridge centrifuge tube and centrifuged at 12,000 rpm for 10 minutes, to thereby remove *E. coli* cells. The supernatant was transferred to another oakridge centrifuge tube, and PEG6000/NaCl (3 mL; PEG=polyethylene glycol) was added thereto, followed by thorough stirring. The resultant mixture was left to stand at 4° C. for 4 hours.

Subsequently, centrifugation was performed at 12,000 rpm for 10 minutes for causing sedimentation of the phages. The supernatant was removed, and the phage sediment was suspended in TBS (1 mL). The suspension was transferred to a 1.5-mL Eppendorf tube and centrifuged at 15,000 rpm for 10 minutes, to thereby remove insoluble substances. The supernatant was transferred to another Eppendorf tube, PEG/NaCl (150 μL) was added thereto, and the mixture was thoroughly stirred and left to stand at 4° C. for 1 hour.

The mixture was centrifuged at 15,000 rpm for 10 minutes, to thereby allow the phages to precipitate. The supernatant was removed, and the precipitated phage pellet was resuspended in TBS (200 μL). The suspension was centrifuged at 15,000 rpm for 10 minutes, to thereby settle insoluble substances. The sediment was transferred to a 0.5-mL Eppendorf tube for storage of the phage clones at 4° C.

Extraction of DNA from the thus-obtained phage clones was performed in the following manner. Phage clones, TBS, and TE-saturated phenol (produced by Nippon Gene Co., Ltd.) were placed in a 1.5-mL Eppendorf tube in amounts of 100 µL, 100 µL, and 200 µL, respectively, and the mixture was violently stirred for 10 minutes, then subjected to centrifugal separation at 15,000 rpm for 10 minutes. Subsequently, TE-saturated phenol (200 µL) and chloroform (200 µL) were added to the supernatant (aqueous phase; 200 µL), and the mixture was violently stirred for 10 minutes, followed by centrifugal separation at 15,000 rpm for 10 minutes. TE (250 µL), 3M sodium acetate (40 µL), 20 mg/mL glycogen (product of Boehringer Mannheim; 1 µL), and ethanol (1 ml) were added to the supernatant (aqueous phase; 150 µL), and the mixture was allowed to stand at −20° C. for one hour in a 1.5-mL Eppendorf tube, followed by centrifugal separation at 15,000 rpm for 10 minutes. The supernatant was discarded, 80% ethanol (−20° C.; 1 mL) was gently added to the residue, and the remaining salts were removed through centrifugal separation at 15,000 rpm for 10 minutes. The supernatant was discarded, moisture within the tube was evaporated, and the DNA that precipitated was dissolved in sterilized distilled water (10 µL) for storage at 4° C.

The thus-obtained phage DNAs were subjected to amino acid sequencing of peptides.

(6) Amino Acid Sequencing of Selected Peptides

The amino acid sequence of a peptide encoded by phage DNA was determined by the dye terminator method using a DNA sequence kit (produced by Perkin Elmer, Code; 402079, Lot; A6L015) in accordance with the manual appended to the kit. The DNA sequence of the primer, shown as SEQ ID NO: 10, was synthesized with an automatic DNA synthesizer.

Elongation reaction for DNA was performed by use of a thermal cycler (Model 9600, Perkin Elmer, 25 cycles, one cycle consisting of 96° C. for 10 seconds, 50° C. for 5 seconds, and 60° C. for 4 minutes). For sequencing of DNA, a DNA sequencer (ABIPRISMTM 377, product of ABI) was employed.

Of the 32 clones, the DNA sequences of 27 clones were successfully determined and classified into 4 types. These 4 types of peptides, taken as GD3-mimetic peptides, were named "GD3R1," "GD3R2," "GD3R3," and "GD3R4 (from the highest to the lowest occurrences).

The amino acid sequences of the thus-determined four species of GD3-mimetic peptides are represented by SEQ ID NOs: 1, 2, 3, and 4, and the DNA sequences coding for these 4 species of amino acids are represented by SEQ ID NOs: 5, 6, 7, and 8.

Example 2

Binding Affinity of GD3-Mimetic Peptide and Anti-GD3 Antibody (ELISA)

A 0.1M NaHCO$_3$ solution containing each of the phage clones obtained in Example 1 ($10^{11}$, $10^{10}$, or $10^9$ titer/100 µL) was added to the wells of a 96-well microtiter plate (product of Nunc), for immobilization of the phage clones at room temperature for one hour. The supernatant was removed, then the wells were subjected to blocking by use of a blocking solution (400 mL; TBS containing 1% BSA, 0.1% skim milk, and 0.02% Tween 20; pH 7.5) at 37° C. for four hours.

The supernatant was removed, then GD3 antibody 4F6 (100 µL), serving as a primary antibody, was added to each well for reaction under shaking at room temperature for two hours. After completion of reaction, the supernatant was removed, then the wells were washed six times with a washing solution (400 µL for each well, TBS containing 0.05% Tween 20). Subsequently, a secondary antibody (anti-mouse IgG-HRP, product of Santa Cruz Biotechnology, catalogue No. SC-2031, Lot. No. C089) which was diluted 5,000-fold by use of a blocking solution prepared in advance was added to the wells (100 µL to each well) for reaction under shaking at room temperature for one hour. After completion of reaction, the wells were washed four times with a washing solution (400 µL for each well), then a detection reagent (TMB Microwell; product of KPL, Catalogue No. 50-76-04, Lot. No. WF075) was added to the wells (100 µL to each well), and the mixture was allowed to stand for five minutes at room temperature.

1N-Hydrochloric acid (100 µL) was added to each well for stopping the reaction. Absorbance of each well was measured at 450 nm and 620 nm, and "OD450-OD620" was calculated. A Multiscan (product of Labosystems) was used in measurement of absorbance. A well in which phages had not been immobilized served as a blank, and the absorbance of each well was determined by subtracting the blank value from the "as-measured" value.

The results are shown in FIG. 1.

FIG. 1 shows that GD3R4 exhibits the strongest binding affinity to GD3 antibody 4F6.

Example 3

Synthesis of GD3-Mimetic Peptide and Binding Affinity to Anti-GD3 Antibody (1) Synthesis of GD3-Mimetic Peptide The four species of GD3-mimetic peptide obtained in Example 1 were synthesized through the following method.

Briefly, by use of an automatic peptide synthesizer (ACT357, product of Advanced Chemtech) along with software of the same company, solid-phase synthesis of respective peptides was performed through the Fmoc/NMP, HOBt method (Fmoc: 9-fluorenylmethoxycarbonyl, NMP: N-methylpyrrolidone, HOBt: 1-hydroxybenzotriazole).

In accordance with the synthesis program, C-terminus-free (OH) peptides were engineered with reference to the amino acid sequences of SEQ ID NOS: 1-4. Specifically, to 0.25 mmol of "Fmoc—amino acid—Alko resin," which corresponded to the C-terminus amino acid of the peptide of interest, Fmoc—amino acids corresponding to the second amino acid (to the C-terminus) and subsequent amino acids were sequentially added for elongation of the chain.

Also, peptides each having a C-terminus amide were engineered as follows. In accordance with the synthesis program, "Fmoc—amino acid," which corresponded to the C-terminus amino acid of the peptide of interest, was added to 0.25 mmol of "Fmoc—NH—SAL resin," to thereby induce condensation reaction therebetween, and subsequently, Fmoc—amino acids corresponding to the second amino acid (to the C-terminus) and subsequent amino acids were sequentially caused to be attached through condensation reaction for elongation of the chain.

After completion of reaction, the N-terminus Fmoc group was deprotected in accordance with the program.

Each of the thus-obtained peptide resins was collected in a minicolumn (product of Assist) made of polypropylene, followed by washing with methanol and drying in vacuum. Through the following procedure, the peptide was cleaved from the resin, and protective groups for the side chains of the peptide were also removed. Briefly, Reagent K (82.5% TFA, 5% phenol, 5% $H_2O$, 5% thioanisole, and 2.5% ethanedithiol) (2 mL) was added to the resin, and reaction was allowed to proceed in the minicolumn for 60 minutes.

Subsequently, the reaction mixture was added dropwise to cold diethyl ether (8 mL), to thereby stop the reaction and allow the peptide to precipitate. Thereafter, the mixture in the minicolumn was washed with TFA (2 mL), cold diethyl ether (5 mL) was added to the mixture, the mixture was centrifuged, and the precipitated pellet was washed with diethyl ether (10 mL) four times. Then the peptide was solubilized with 50% acetonitrile (about 5 mL) and freeze-dried. This procedure (solubilization and freeze-dring) was repeated twice, whereby a crude freeze-dried product of interest was obtained.

The freeze-dried product was fractionated by means of reversed-phase high-performance liquid chromatography (HPLC) employing an Octadecyl Column (20 (diameter)× 250 mm, product of YMC), to thereby isolate the peptide of interest.

The resins and the amino acid derivative which were used in the above-described procedure are products of Watanabe.

The thus-isolated respective peptides were identified through amino acid sequencing and molecular weight measurement through mass spectrometry.

(2) Synthesis of Multi-Antigen Peptide

Multi-antigen peptides of the above-obtained GD3-mimetic peptides (MAPs) were synthesized by use of an Fmoc—MAP—Alko resin (product of Watanabe).

Reaction between the Fmoc—MAP—Alko resin ($Fmoc_8$-$Lys_4$-$Lys_2$-Lys-βAla-Alko resin (SEQ ID NO:11)) and each of the GD3-mimetic peptides proceeded in the same manner as the above-described solid-phase synthesis method.

The structures of the thus-obtained MAPs, shown by one letter representation of amino acid residues, are as follows.

MAP of SEQ ID NO: 1 peptide:
(LAPPRPRSELVFLSV)$_8$-Lys$_4$-Lys$_2$-Lys-βAla (SEQ ID NO:12)

MAP of SEQ ID NO: 2 peptide:
(PHFDSLLYPCELLGC)$_8$-Lys$_4$-Lys$_2$-Lys-βAla (SEQ ID NO: 13)

MAP of SEQ ID NO: 3 peptide:
(GLAPPDYAERFFLLS)$_8$-LYS$_4$-LYS$_2$-LYS-βAla (SEQ ID NO:14)

MAP of SEQ ID NO: 4 peptide:
(RHAYRSMAEWGFLYS)$_8$-LYS$_4$-LYS$_2$-LYS-βAla (SEQ ID NO:15)

(3) Binding Affinity to Anti-GD3 Antibody

A 0.1M $NaHCO_3$ solution containing a GD3-mimetic peptide of the invention in the above MAP form (100 ng/100 μL) was added to the wells of a 96-well micro-titer plate, for immobilization at room temperature for one hour. Subsequently, in a manner similar to the ELISA method employed in Example 2, binding affinity of the GD3-mimetic peptide to GD3 antibody 4F6 was investigated.

Anti-GD2 antibody and anti-OAcGD3 antibody (Cerato, E., et al., Hybridoma, 16(4), 307-316 (1997)) were used as controls (these antibodies were kindly provided by from Dr. Portoukalian).

The results are shown in Table 2 below.

TABLE 2

| Serum % | 100% | 50% | 25% | 12.50% |
|---|---|---|---|---|
| Anti-GD3 antibody | | | | |
| GD3R1 | 0.263 | 0.137 | 0.127 | 0.083 |
| GD3R2 | 0.264 | 0.159 | 0.105 | 0.055 |
| GD3R3 | 0.483 | 0.357 | 0.237 | 0.176 |
| GD3R4 | 0.381 | 0.309 | 0.229 | 0.144 |
| Anti-GD2 antibody | | | | |
| GD2R1 | 0.123 | 0.095 | 0.067 | 0.065 |
| GD2R2 | 0.132 | 0.079 | 0.071 | 0.052 |
| GD2R3 | 0.191 | 0.036 | 0.118 | 0.077 |
| GD2R4 | 0.149 | 0.103 | 0.072 | 0.061 |
| Anti-OAcGD3 antibody | | | | |
| GD3R1 | 0.053 | 0.046 | 0.041 | 0.04 |
| GD3R2 | 0.038 | 0.027 | 0.023 | 0.021 |
| GD3R3 | 0.044 | 0.031 | 0.026 | 0.031 |
| GD3R4 | 0.061 | 0.047 | 0.043 | 0.045 |

As is apparent from Table 2, among other mimetic peptides, GD3R3 and GD3R4 exhibit stronger bonding to the anti-GD3 antibody. In addition, all the peptides were found to bind to the anti-GD3 antibody stronger than to the control antibodies.

(4) Synthesis of Fusion Peptide

Fusion peptides—fused with KLH—were prepared by use of each of the above-obtained GD3-mimetic peptides or an MAP thereof.

Briefly, each of the above-synthesized peptides, or an MAP thereof, and KLH were added to a PBS solution (pH 7.4) containing 0.25% glutaraldehyde at a ratio by weight of 1:10, and the mixture was allowed to react overnight at room temperature, to thereby synthesize a fusion peptide.

Example 4

Immunization by Use of GD3-Mimetic Peptide (1) Immunization:

Four species of GD3-mimetic peptide (MAP) obtained in Example 3 (2) was dissolved in PBS so as to attain a concentration of 200 μg/mL. The solution was added to Freund's complete (or incomplete) adjuvant (1:1, by volume), to thereby prepare an emulsion.

Eight mice (C57BL/6) were immunized by subcutaneous administration of the above emulsion (0.2 mL/mouse, in one administration, 5 μg peptide per mouse). Administration was performed every two weeks (for the second and subsequent administrations, Freund's incomplete adjuvant was used). After one week following respective administrations, blood was collected from the tail of each mouse, to thereby yield antiserum.

The antiserum obtained directly after the first administration will be referred to "1-st," that obtained after the second administration will be referred to "2-nd," and that obtained after the third administration will be referred to "3-rd."

(2) Titer Measurement of Antiserum (ELISA):

The titer, against GD3, of each of the antiserum samples (3×8 mice=24 samples) obtained in the (1) above was measured through ELISA as described below.

GD3 employed in the test was kindly provided by Dr. Portoukalian, and was a product extracted from melanoma and purified (J. Portoukalian et al., Int. Cancer, 49, 893-899

(1991)). GD3 was purified by means of HPLC employing a silica gel (Si60) column (product of Merck, U.S.A.) in a chromatogram (Hitachi L-6200). GD3 that had adsorbed onto the column wall was eluted with a mixture of isopropanol/hexane/purified water (with a gradient from 55/35/12 to 55/30/15 by volume). The flow rate in the column was 4 mL per minute.

The thus-obtained purified GD3 was dissolved in methanol, whereby a GD3 solution having a concentration of 10 µg/mL was prepared. The GD3 solution was added to the wells of a 96-well micro-titer plate in amounts of 10 µL per well (which corresponds to 100 ng GD3 per well), and methanol was evaporated. Subsequently, a blocking solution (TBS supplemented with 1% BSA) was added to the wells in amounts of 50 µL per well, for blocking at 37° C. for 4 hours.

The supernatant was discarded. Each of the antiserum samples obtained in (1) above was diluted 100-fold, 400-fold, or 1,600 fold with the above-mentioned blocking solution. The diluted antiserum (50 µL) was added to each well for reaction at 4° C. overnight. The well was washed six times with TBS, and thereafter, HRP-labeled mouse IgG antibody diluted 5,000-fold with the blocking solution was added (50 µL per well) for reaction for 2 hours at room temperature. The well was washed four times with TBS, and thereafter, enzymatic activity (peroxidase) of the well was detected with TMB solution (50 µL). The reaction was stopped with 1N HCl (50 µL), and the value corresponding to "420 nm-620 nm" was calculated.

A control sample was prepared as follows. Firstly, an irrelevant peptide (i.e., a peptide of 15 amino acid residues which is different from any of the four peptides obtained in Example 1 and which does not have binding affinity with anti-GD3 antibody; the sequence is represented by SEQ ID NO: 10) was synthesized in a manner similar to that employed in Example 3. The synthesized peptide was administered to a mouse for immunization, and the obtained antiserum served as a control sample. The titer of the control sample was obtained in a manner similar to that described above. (However, the number of provided mice was five, and only a 100-fold diluted solution was used.) This control peptide sample was also used in the form of MAP as described above.

Reactivity data of respective antiserum samples with GD3 are summarized in Tables 3 to 5 below.

TABLE 3

| Sample No. | GD3R-1 Dilution factor | | | Sample No. | GD3R-2 Dilution factor | | |
|---|---|---|---|---|---|---|---|
| | 1/100 | 1/400 | 1/1600 | | 1/100 | 1/400 | 1/1600 |
| 1-1st | 0.034 | 0.017 | 0.004 | 1-1st | 0.316 | 0.252 | 0.179 |
| 2nd | 0.082 | 0.026 | 0.01 | 2nd | 0.34 | 0.241 | 0.13 |
| 3rd | 0.023 | 0.01 | 0.003 | 3rd | 0.113 | 0.099 | 0.036 |
| 2-1st | 0.052 | 0.039 | 0.007 | 2-1st | 0.062 | 0.035 | 0.022 |
| 2nd | 0.087 | 0.027 | 0.016 | 2nd | 0.183 | 0.078 | 0.039 |
| 3rd | 0.068 | 0.019 | 0 | 3rd | 0.08 | 0.075 | 0.023 |
| 3-1st | 0.047 | 0.026 | 0 | 3-1st | 0.042 | 0.031 | 0.053 |
| 2nd | 0.14 | 0.063 | 0.022 | 2nd | 0.135 | 0.049 | 0.035 |
| 3rd | 0.066 | 0.017 | 0.002 | 3rd | 0.053 | 0.053 | 0.014 |
| 4-1st | 0.106 | 0.057 | 0.005 | 4-1st | 0.114 | 0.068 | 0.028 |
| 2nd | 0.188 | 0.088 | 0.034 | 2nd | 0.142 | 0.071 | 0.025 |
| 3rd | 0.084 | 0.03 | 0.008 | 3rd | 0.057 | 0.084 | 0.008 |
| 5-1st | 0.03 | 0.024 | 0 | 5-1st | 0.087 | 0.05 | 0.045 |
| 2nd | 0.102 | 0.074 | 0.019 | 2nd | 0.131 | 0.034 | 0.016 |
| 3rd | 0.139 | 0.054 | 0.003 | 3rd | 0.184 | 0.161 | 0.053 |
| 6-1st | 0.055 | 0.052 | 0.008 | 6-1st | 0.155 | 0.078 | 0.028 |
| 2nd | 0.117 | 0.047 | 0.019 | 2nd | 0.115 | 0.091 | 0.033 |
| 3rd | 0.084 | 0.021 | 0.001 | 3rd | 0.09 | 0.089 | 0.028 |
| 7-1st | 0.059 | 0.034 | 0 | 7-1st | 0.076 | 0.055 | 0.014 |
| 2nd | 0.168 | 0.06 | 0.014 | 2nd | 0.072 | 0.039 | 0.016 |
| 3rd | 0.121 | 0.051 | 0.004 | 3rd | 0.05 | 0.059 | 0.012 |
| 8-1st | 0.061 | 0.027 | 0.016 | 8-1st | 0.084 | 0.044 | 0.034 |
| 2nd | 0.054 | 0.039 | 0.024 | 2nd | 0.069 | 0.047 | 0.034 |
| 3rd | 0.08 | 0.03 | 0 | 3rd | 0.098 | 0.086 | 0.023 |

TABLE 4

| Sample No. | GD3R-3 Dilution factor | | | Sample No. | GD3R-4 Dilution factor | | |
|---|---|---|---|---|---|---|---|
| | 1/100 | 1/400 | 1/1600 | | 1/100 | 1/400 | 1/1600 |
| 1-1st | 0.062 | 0.071 | 0.015 | 1-1st | 0.086 | 0.032 | 0.007 |
| 2nd | 0.08 | 0.054 | 0.024 | 2nd | 0.122 | 0.058 | 0.019 |
| 3rd | 0.047 | 0.022 | 0.016 | 3rd | 0.116 | 0.053 | 0.013 |
| 2-1st | 0.169 | 0.083 | 0.017 | 2-1st | 0.042 | 0.021 | 0.014 |
| 2nd | 0.116 | 0.078 | 0.025 | 2nd | 0.08 | 0.07 | 0.022 |
| 3rd | 0.126 | 0.039 | 0.027 | 3rd | 0.088 | 0.042 | 0.008 |
| 3-1st | 0.105 | 0.077 | 0.009 | 3-1st | 0.071 | 0.047 | 0.014 |
| 2nd | 0.098 | 0.079 | 0.025 | 2nd | 0.164 | 0.114 | 0.026 |
| 3rd | 0.143 | 0.032 | 0.026 | 3rd | 0.176 | 0.093 | 0.029 |
| 4-1st | 0.062 | 0.004 | 0.016 | 4-1st | 0.247 | 0.108 | 0.052 |
| 2nd | 0.08 | 0.112 | 0.034 | 2nd | 0.195 | 0.128 | 0.062 |
| 3rd | 0.069 | 0.028 | 0.018 | 3rd | 0.253 | 0.111 | 0.026 |
| 5-1st | 0.098 | 0.048 | 0.006 | 5-1st | 0.086 | 0.033 | 0.009 |
| 2nd | 0.165 | 0.118 | 0.022 | 2nd | 0.153 | 0.093 | 0.033 |
| 3rd | 0.189 | 0.073 | 0.017 | 3rd | 0.19 | 0.104 | 0.022 |
| 6-1st | 0.051 | 0.016 | 0.023 | 6-1st | 0.08 | 0.041 | 0.008 |
| 2nd | 0.132 | 0.088 | 0.027 | 2nd | 0.124 | 0.106 | 0.031 |
| 3rd | 0.189 | 0.033 | 0.018 | 3rd | 0.168 | 0.098 | 0.039 |
| 7-1st | 0.04 | 0.026 | 0.003 | 7-1st | 0.063 | 0.034 | 0.006 |
| 2nd | 0.135 | 0.076 | 0.018 | 2nd | 0.147 | 0.079 | 0.041 |
| 3rd | 0.073 | 0.03 | 0.013 | 3rd | 0.113 | 0.045 | 0.013 |
| 8-1st | 0.165 | 0.067 | 0.031 | 8-1st | 0.082 | 0.037 | 0.012 |
| 2nd | 0.179 | 0.088 | 0.07 | 2nd | 0.05 | 0.057 | 0.013 |
| 3rd | 0.098 | 0.023 | 0.018 | 3rd | 0.147 | 0.061 | 0.024 |

TABLE 5

| Sample No. | Control peptide Dilu. factor 1/100 |
|---|---|
| 1-1st | 0.105 |
| 2nd | 0.064 |
| 3rd | 0.006 |
| 2-1st | 0.088 |
| 2nd | 0.056 |
| 3rd | 0 |
| 3-1st | 0.057 |
| 2nd | 0.042 |
| 3rd | 0.007 |
| 4-1st | 0.041 |
| 2nd | 0.028 |
| 3rd | 0.004 |
| 5-1st | 0.051 |
| 2nd | 0.031 |
| 3rd | 0.031 |

As is apparent from form Tables 3 to 5, the antiserum samples obtained through use, as an immunogen, of a GD3-mimetic peptide of the present invention cross-react with GD3; in particular, those obtained through use, as an immunogen, of a GD3R4 of the present invention exhibit high reactivity with GD3. In contrast, antiserum samples obtained through use of the control peptide was found to exhibit weak reactivity with GD3, and taken together, antisera obtained through use of a GD3-mimetic peptide of the present invention are suggested to cross-react with GD3.

The above results suggest that GD3-mimetic peptides of the present invention, in particular GD3R4, mimic a portion of the structure of GD3; i.e., a structural portion recognized by anti-GD3 antibody 4F6.

Example 5

Reactivity of GD3-Mimetic Peptide (1) In a manner similar to that described in Example 3, peptides of N-terminus 9 amino acid residues or C-terminus 9 amino acid residues of GD3R1, GD3R2, GD3R3, or GD3R4. The nomenclature and sequences of respective peptides employed in the present test are shown in FIG. 2 These were employed as multi-antigen peptides (MAPs).

(2) In order to extend the research on bonding between the anti-GD3 antibody 4F6 and each of the GD3-mimetic peptides shown in FIG. 1, multi-antigen peptides (MAPs) were subjected to ELISA. MAP samples having a variety of concentrations shown on the X-axis in FIG. 3 were provided, and each sample was immobilized onto the wells of a 96-well plate. Subsequently, the wells were blocked with a blocking solution (TBS supplemented with 1% BSA, 0.1% skim milk, and 0.02% Tween 20) at 4° C. overnight. 4F6 (hybridoma supernatant: used in the neat form) was added (100 μL/well) for reaction at room temperature for 2 hours. After completion of reaction, the supernatant was discarded, and the wells were washed with a washing solution (TBS supplemented with 1% FBS and 0.05% Tween 20) six times. Subsequently, the wells were allowed to react with peroxidase-labeled anti-mouse IgG (diluted 1,000-fold with a blocking solution) at room temperature for 2 hours. The wells were again washed with a washing solution four times, and the amount of peroxidase enzyme remaining in each well was detected and quantitatively determined with the substrate TMB, whereby binding of MAP to 4F6 was investigated. The test was performed in triplicate, and the values in the graph are "mean±SD."

Figure 3:
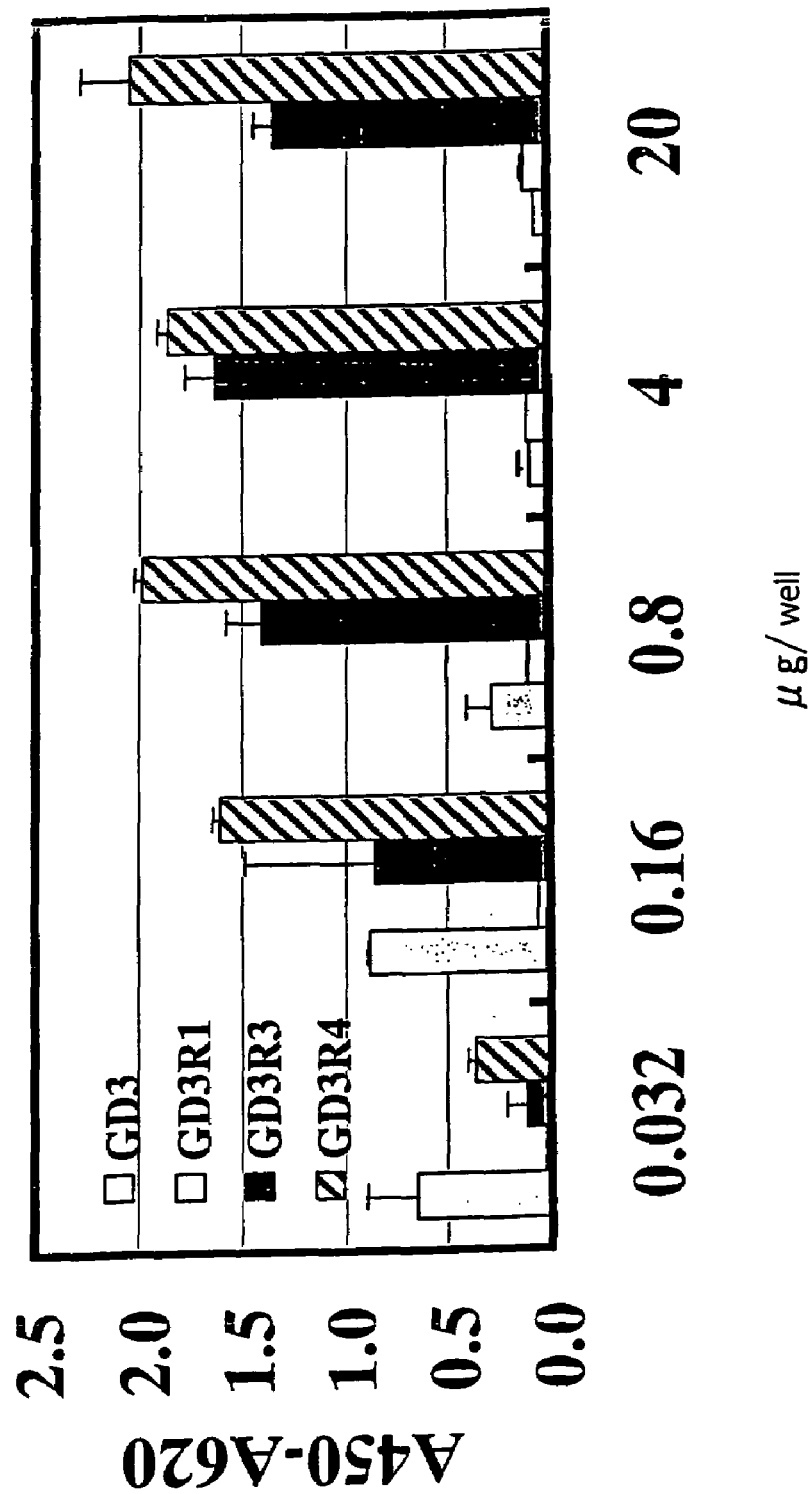
FIG. 3 is a graph showing binding affinity of GD3-mimetic peptides and anti-GD3 monoclonal antibody.

As understood from FIG. 3, 4F6 binds to GD3-mimetic peptides 3 or 4 in an amount-dependent manner. Although bonding to GD3 appears to have declined from the concentration 0.8 μg/well and higher, this may be attributed to excessive amount of immobilized GD3 present on the ELISA plate, which intensified hydrophobicity, thereby inhibiting binding to the antibody.

(3) The binding affinity shown in FIG. 3 was investigated in another method. Briefly, MAP samples having a variety of concentrations shown on the X-axis in FIG. 4 were provided. Each sample was immobilized onto the wells of a 96-well plate, and the wells were allowed to react with 4F6 (100 μL/well) at 4° C. overnight. On the following day, the supernatant (80 μL) was collected and added to the wells of another plate to which GD3 had been immobilized in advance (100 ng/well) for reaction at room temperature for 2 hours. After completion of reaction, the amount of antibody 4F6 that had been condensed with GD3 (i.e., that had not been absorbed by MAP) was detected and quantitatively determined through the method described (2) above, whereby inhibitory effect of MAP on binding of GD3 to 4F6 was investigated. The test was performed in triplicate, and the values in the graph are "mean±SD."

Figure 4:
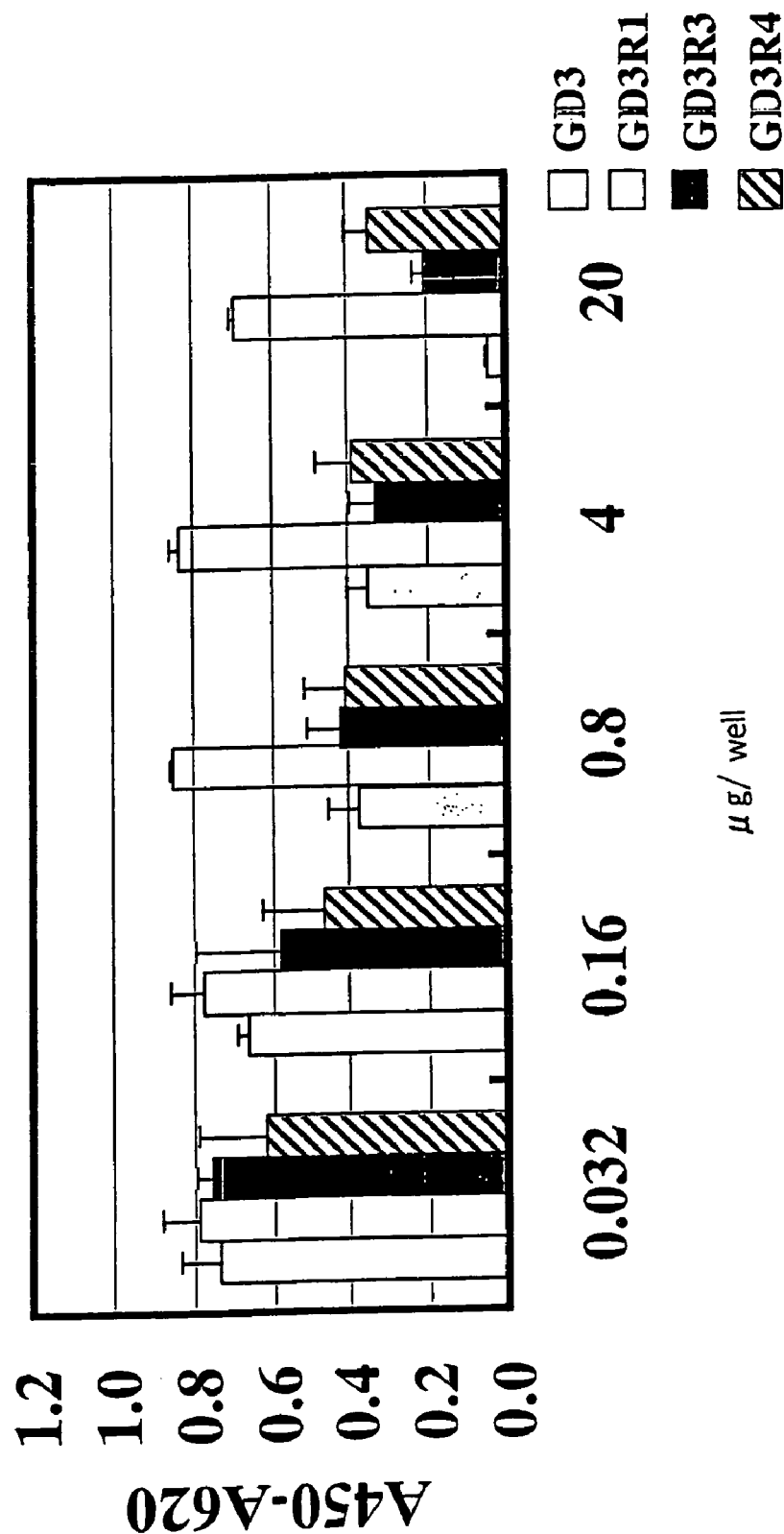
FIG. 4 is a graph showing inhibitory effect exerted by immobilized GD3-mimetic peptides against binding between GD3 and 4F6 (anti-GD3 antibody).

As a result, as shown in FIG. 4, like the case of GD3, both the GD3-mimetic peptides 3 and 4 were found to inhibit GD3 from binding to the antibody, and the inhibition occurred in a manner dependent on the amount immobilized.

(4) Next, investigation was made as to whether binding between GD3R3 or GD3R4 and 4F6 occurred at the GD3 binding site of 4F6. To the wells of a plate to which GD3 had been immobilized (100 μg/well), each of the MAP samples having a variety of concentrations shown on the X-axis in FIG. 5 and 4F6 (100 μL/well) were simultaneously added, whereby an inhibitory test was performed. The test was performed in triplicate, and the values in the graph are "mean±SD."

Figure 5:
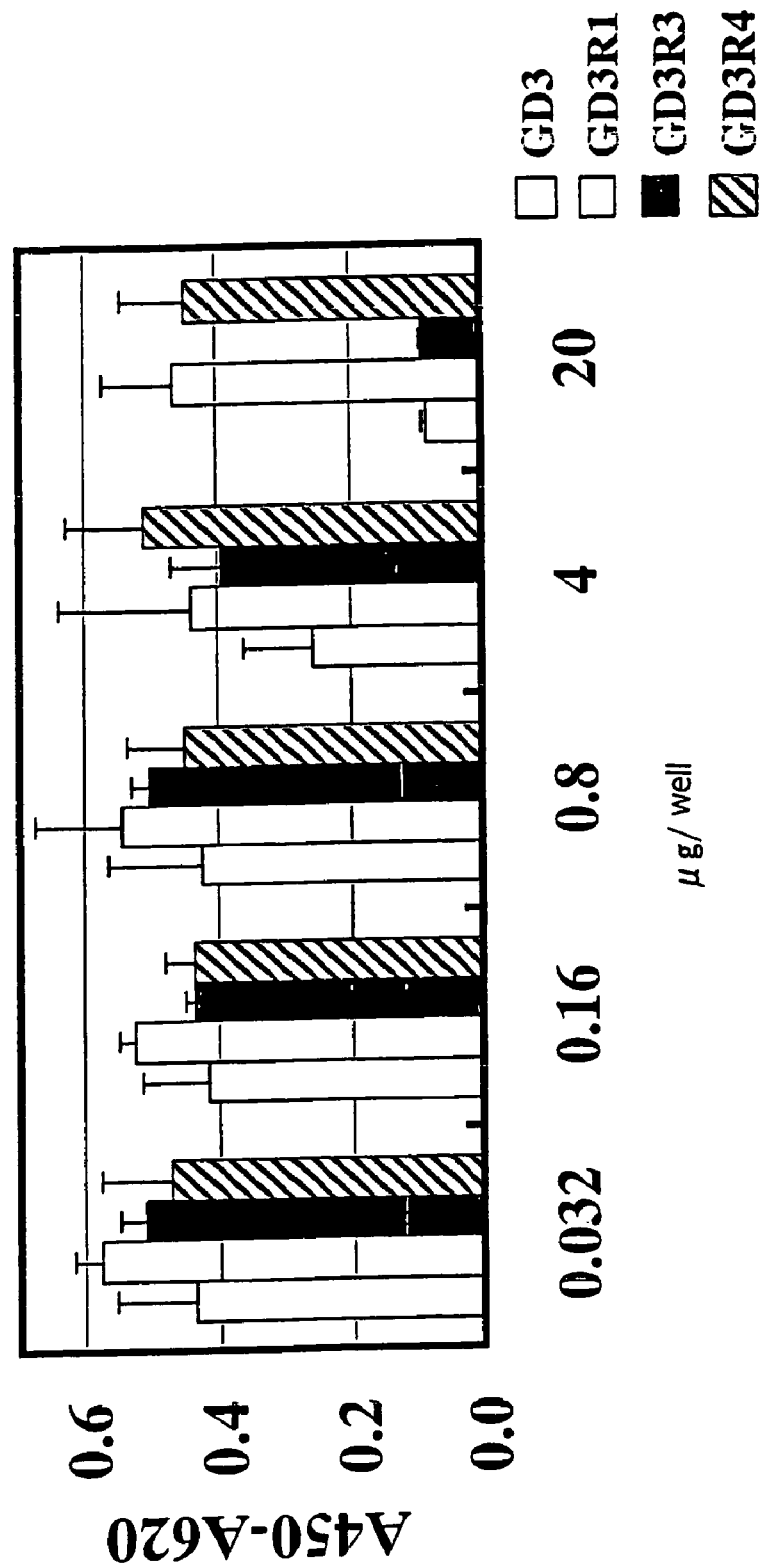
FIG. 5 is a graph showing inhibitory effect exerted by exogenously added GD3-mimetic peptides against binding between GD3 and 4F6.

As a result, as is apparent from FIG. 5, within the concentration range employed in the present test, GD3R3, like GD3, exhibited inhibitory effect, but R4 did not. From these results, the following two are deduced. Firstly, the binding strength between 4F6 and respective MAPs decreases in the order of GD3>GD3R3>GD3R4. Secondly, GD3R3 is bound to the GD3 binding site, or in the vicinity, of 4F6.

(5) Through the procedure described above, among other mimetic peptides, GD3R3 has been found to specifically bind to the GD3-binding domain of 4F6 or a site close thereto. Next, in an attempt to determine the domain required for establishing binding to anti-GD3 antibody 4F6 in GD3-mimetic peptides, an MAP of nine N-terminus residues of GD3R3 peptide and an MAP of nine C-terminus residues of the same GD3R3 peptide as shown in FIG. 2 were synthesized, their binding to 4F6 was studied by means of ELISA. ELISA was performed was performed in triplicate, and the values in the graphs are "mean±SD."

Figure 6:
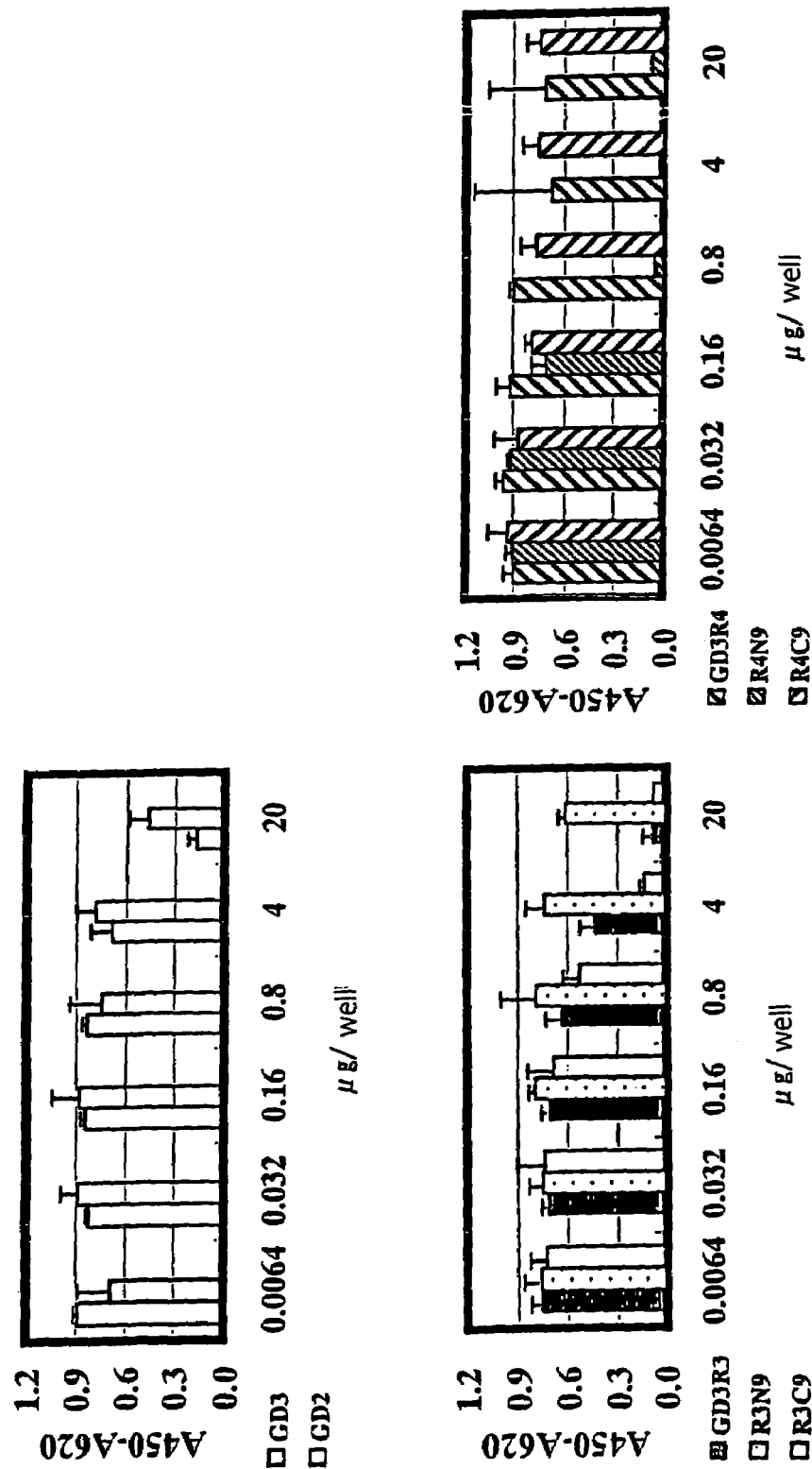
FIG. 6 is a graph showing inhibitory effect exerted by exogenously added GD3-mimetic peptides (nine residues) against binding between GD3 and 4F6.

As a result, as is apparent from FIG. 6, GD3R3C9 was found to have comparable ability to the 15 residues in inhibiting binding between GD3 and 4F6, and the inhibition occurred in a manner dependent on the amount immobilized.

Taken together, it has become clear that GD3R3 is the strongest in binding to anti-GD3 antibody 4F6, and that nine residues from the C-terminus (GD3R3C9) is critical in establishing binding.

Example 6

Immunization with Fusion Peptide (1) Immunization

Using a fusion peptide R4-KLH obtained in Example 3(4) between GD3R4 and KLH or a MAP form fusion peptide R4MAP-KLH created between GD3R4 and KLH, immunization was performed as described in (1) above.

Briefly, an emulsion mixed with an adjuvant (1:1, by volume) was administered to each member of groups of mice, each group consisting of 3 mice (CD-1), in an amount of 100 μL/mouse (for one administration (ip), peptide 30 μg/mouse) for immunization. In the case of R4-KLH, administration was performed every one week for one month, and subsequently every two weeks for one month; and in the case of R4MAP-KLH, every one week for 2 months. In any case, 4 days after the final immunization, blood was collected to thereby prepare antiserum samples.

Similar to the case of immunization with R4-KLH, antiserum samples were also prepared through immunization with GD3 (30 μg).

(2) ELISA Test

Through use of an ELISA plate to which GD3 or GD3R4 peptide had been immobilized, the procedure described in Example 4(2) was repeated.

GD3-Immobilized plate: GD3 in methanol-PBS (1:1) (0.5 μg/50 μL) was added to each well, and the plate was left to stand for one hour. The wells were washed with PBS, then 1% HSA in PBS was added thereto (200 μL/well) for incubation at 37° C. for 2 hours, whereby the wells were blocked.

GD3R4 Peptide immobilized plate: GD3R4 peptide (1 μg) dissolved in 0.1M bicarbonate buffer (pH 9.5) was added to each well, followed by incubation at 37° C. overnight and washing with PBS, whereby the wells were blocked in a manner similar to the above.

The antiserum samples obtained in the above were diluted with PBS to thereby yield 100-fold to 10,000-fold diluted antiserum samples. Each of the resultant diluted antiserum samples (50 μL) was added to each well and the mixture was allowed to react for one hour. Subsequently, reaction was allowed to proceed with biotinylated anti-mouse immunoglobulin antibody (Ig, IgM, IgG, IgG1, IgG2a, IgG2b or IgG3 specific antibody) for one hour, then with streptoavidin-HRP for one hour in a similar manner, after which enzymatic activity in each well was detected as described above (405 nm).

(3) Cell Response Test

The spleen aseptically removed from each of the above-immunized mice was minced in a 10% FCS-supplemented RPMI 1640 medium. By use of a nylon wool column, T-cell-rich lymphocytes were prepared and the cells were counted. The above medium containing the cells in an amount of $10^5$ cells per 150 μL was added to each of the wells of a culture plate. PHA was added so as to attain a final concentration of 1 μg/mL. A peptide of the present invention or any of different gangliosides in PBS was added, and the mixture was incubated for 96 hours. A supernatant (100 μL) was obtained from each well. The IL-2 activity of the supernatant was determined through use of IL-2-dependent mouse cells, CTLL2. Briefly, the supernatant (100 μL) diluted 2 to 50-fold with a medium was added to the wells in an amount of $10^4$ CTLL2 cells/well, followed by incubation at 37° C. for 48 hours. Subsequently, 3H-thymidine (0.5 μCi) was added to each well, followed by incubation for 6 hours. CTLL2 cells were recovered on a paper filter and counted for 3H.

(4) Results

Figure 7:
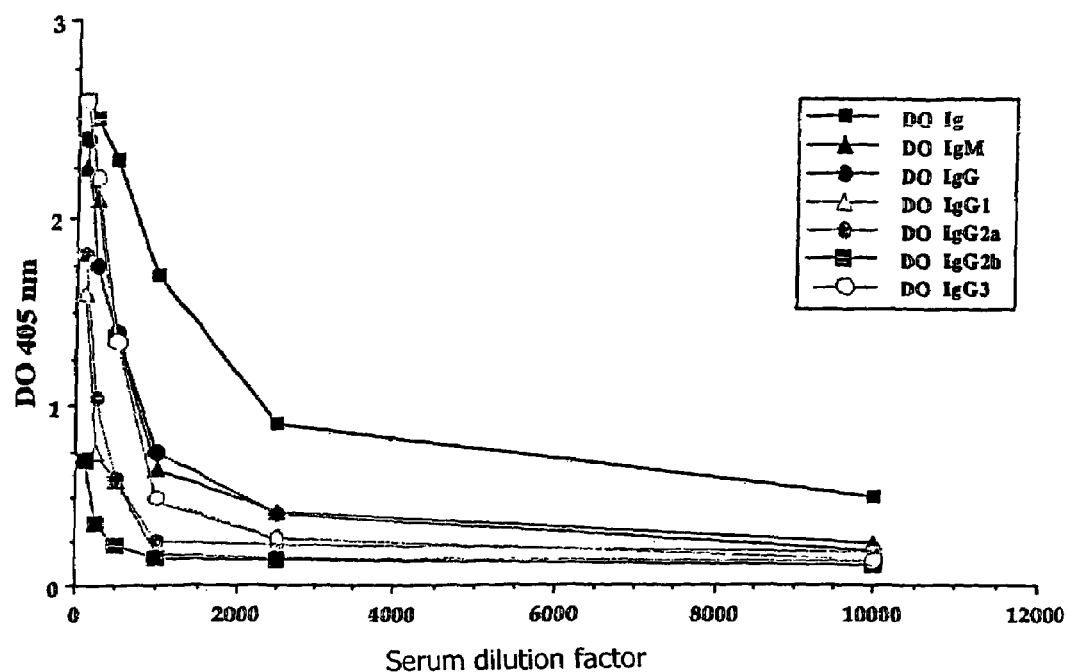
FIG. 7 is a graph showing the relationship between dilution factor of serum samples from mice immunized with peptide R4 and results of ELISA on GD3.
Figure 8:
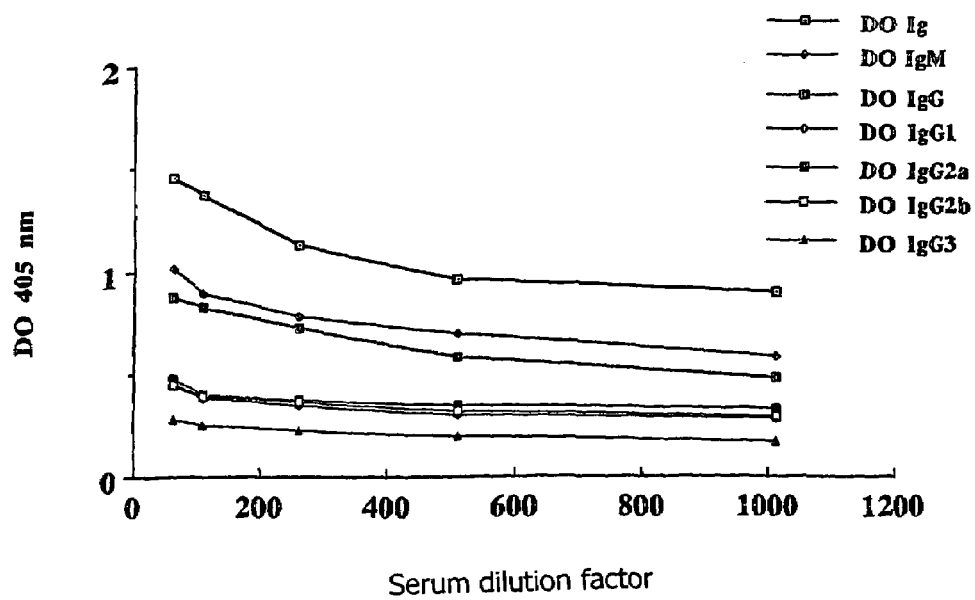
FIG. 8 is a graph showing the relationship between dilution factor of serum samples from mice immunized with R4MAP for two months and results of ELISA on GD3.
Figure 9:
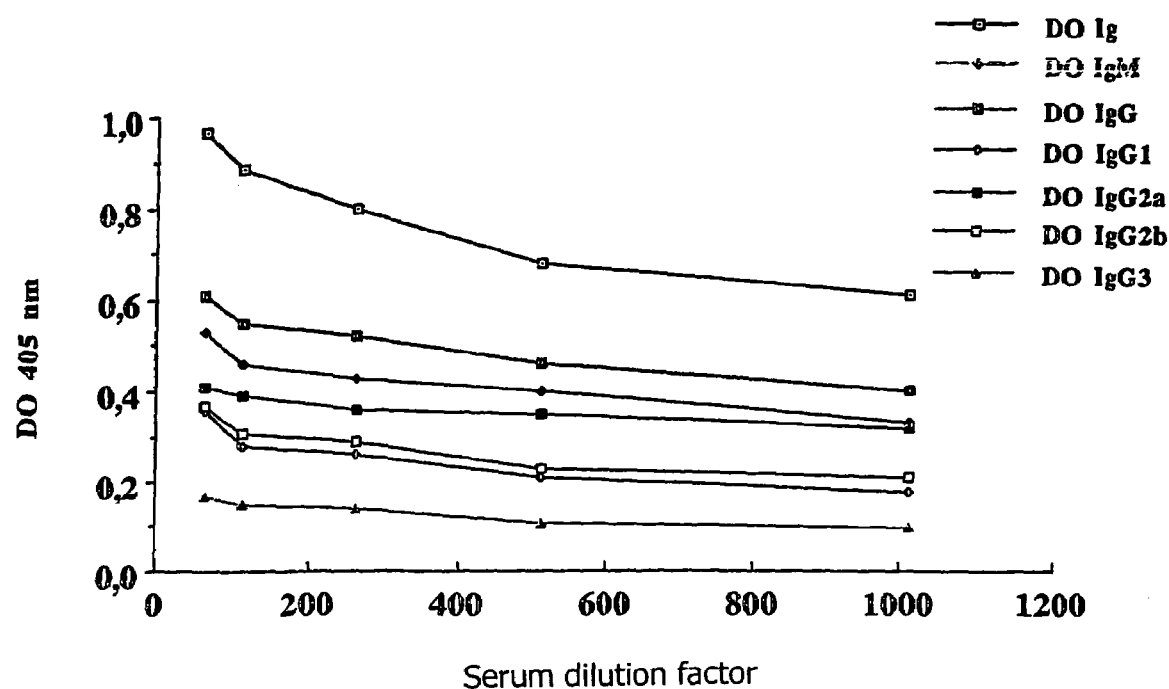
FIG. 9 is a graph showing the relationship between dilution factor of serum samples from mice immunized with R4MAP for two months and results of ELISA performed on R4MAP peptide.

Antiserum samples obtained from immunization with either R4-KLH or R4MAP-KLH were found to contain specific antibodies that react with both the GD3R4 peptide and GD3. The titers of IgG antibodies and that of IgM antibodies were almost the same. The results regarding reactivity between GD3 and antiserum obtained from immunization with R4-KLH are shown in FIG. 7. Reactivity between GD3 and antiserum obtained from immunization with R4MAP-KLH and reactivity between GD3 and antiserum obtained from immunization with GD3R4 are shown in FIGS. 8 and 9, respectively.

T-cell-rich lymphocytes from GD3-immunized mouse are considered not activated, because IL-2 activity was not detected in the presence of gangliosides (Table 6). However, in the presence of GD3R4 peptide or GD3R3 peptide, production of IL-2 has been confirmed (Table 6). In this connection, in R4-KLH-immunized mice, T cells have been confirmed to have activated by GD3R4 peptide or GD3R3 peptide (Table 7). These results indicate that the peptides of the present invention induce activation of specific T cells in GD3-immunized mice.

TABLE 6

3H Thymidine up-take into IL-R-dependent CTLL2 cells incubated in culture supernatant of spleen cells of mice immunized with GD3 and stimulated with PHA for 96 hours (in the presence of a variety of gangliosides or peptides)

| Stimulation | Dilution factor of culture supernatant | | | |
|---|---|---|---|---|
| (PHA 1 μg/mL+) | 1/2 | 1/5 | 1/20 | 1/50 |
| PHA alone | 2631 ± 248 | 1797 ± 169 | 804 ± 82 | 183 ± 19 |
| GD3 (0.5 μg/ml) | 2795 ± 175 | 1876 ± 152 | 810 ± 72 | 207 ± 22 |
| GD3 (1 μg/ml) | 2568 ± 235 | 1834 ± 169 | 762 ± 55 | 186 ± 27 |
| GD3 (2 μg/ml) | 2453 ± 264 | 1901 ± 188 | 758 ± 61 | 197 ± 28 |
| GD3 (5 μg/ml) | 2656 ± 257 | 1857 ± 185 | 794 ± 68 | 179 ± 23 |
| GM3 (0.5 μg/ml) | 2567 ± 248 | 1897 ± 190 | 824 ± 81 | 182 ± 22 |
| GM3 (1 μg/ml) | 2792 ± 218 | 1728 ± 157 | 833 ± 90 | 178 ± 24 |
| GM3 (2 μg/ml) | 2725 ± 232 | 1824 ± 163 | 859 ± 82 | 181 ± 28 |
| GM3 (5 μg/ml) | 2658 ± 247 | 1751 ± 183 | 832 ± 81 | 179 ± 22 |
| GM1 (0.5 μg/ml) | 2754 ± 282 | 1841 ± 167 | 804 ± 84 | 182 ± 19 |
| GM1 (1 μg/ml) | 2649 ± 255 | 1748 ± 181 | 825 ± 77 | 175 ± 27 |
| GM1 (2 μg/ml) | 2842 ± 248 | 1697 ± 190 | 783 ± 81 | 167 ± 21 |
| GM1 (5 μg/ml | 2737 ± 264 | 1754 ± 184 | 756 ± 76 | 182 ± 26 |
| peptide R4 (1 μg/ml) | 5867 ± 1213 | 3418 ± 749 | 1994 ± 348 | 881 ± 127 |
| peptide R4 (2 μg/ml) | 12671 ± 1643 | 8349 ± 1014 | 3248 ± 613 | 1274 ± 156 |
| peptide R4 (5 μg/ml) | 14237 ± 1884 | 11358 ± 1563 | 7526 ± 839 | 2684 ± 387 |
| peptide R1 (1 μg/ml) | 3014 ± 671 | 1967 ± 276 | 888 ± 107 | 234 ± 43 |
| peptide R1 (2 μg/ml) | 3219 ± 546 | 1831 ± 259 | 906 ± 121 | 246 ± 38 |
| peptide R1 (5 μg/ml) | 3344 ± 497 | 1956 ± 285 | 942 ± 116 | 251 ± 44 |
| peptide R2 (1 μg/ml) | 2957 ± 326 | 1784 ± 164 | 792 ± 88 | 185 ± 31 |
| peptide R2 (2 μg/ml) | 3057 ± 321 | 1719 ± 184 | 856 ± 107 | 192 ± 40 |
| peptide R2 (5 μg/ml) | 3022 ± 316 | 1717 ± 198 | 931 ± 124 | 203 ± 36 |
| peptide R3 (1 μg/ml) | 4066 ± 853 | 2654 ± 486 | 1153 ± 246 | 571 ± 104 |

TABLE 6-continued

3H Thymidine up-take into IL-R-dependent CTLL2
cells incubated in culture supernatant of spleen cells of
mice immunized with GD3 and stimulated with PHA for 96 hours
(in the presence of a variety of gangliosides or peptides)

| Stimulation | Dilution factor of culture supernatant | | | |
|---|---|---|---|---|
| (PHA 1 μg/mL+) | 1/2 | 1/5 | 1/20 | 1/50 |
| peptide R3 (2 μg/ml) | 5791 ± 1154 | 3243 ± 634 | 1540 ± 467 | 749 ± 118 |
| peptide R3 (5 μg/ml) | 7536 ± 1247 | 3528 ± 543 | 1566 ± 328 | 761 ± 102 |

The values are mean ± SE (4 wells)

TABLE 7

3H Thymidine up-take into IL-2-dependent CTLL2
cells incubated in culture supernatant of spleen cells of
mice immunized with R4 peptide and stimulated with PHA for 96
hours (in the presence of a variety of gangliosides or
peptides)

| Stimulation | Dilution factor of culture supernatant | | | |
|---|---|---|---|---|
| (PHA 1 μg/mL+) | 1/2 | 1/5 | 1/20 | 1/50 |
| PHA alone | 2732 ± 255 | 1628 ± 147 | 813 ± 96 | 164 ± 28 |
| GD3 (0.5 μg/ml) | 2635 ± 308 | 1792 ± 154 | 850 ± 87 | 169 ± 25 |
| GD3 (1 μg/ml) | 2721 ± 284 | 1658 ± 134 | 794 ± 82 | 202 ± 24 |
| GD3 (2 μg/ml) | 2797 ± 295 | 1722 ± 163 | 809 ± 74 | 212 ± 28 |
| GD3 (5 μg/ml) | 2619 ± 316 | 1636 ± 145 | 764 ± 68 | 184 ± 23 |
| GM3 (0.5 μg/ml) | 2741 ± 279 | 1683 ± 167 | 812 ± 84 | 167 ± 21 |
| GM3 (1 μg/ml) | 2814 ± 321 | 1728 ± 181 | 873 ± 90 | 194 ± 25 |
| GM3 (2 μg/ml) | 2754 ± 286 | 1619 ± 155 | 768 ± 83 | 157 ± 22 |
| GM3 (5 μg/ml) | 2631 ± 264 | 1587 ± 163 | 729 ± 89 | 152 ± 26 |
| GM1 (0.5 μg/ml) | 2750 ± 317 | 1683 ± 178 | 801 ± 93 | 204 ± 25 |
| GM1 (1 μg/ml) | 2812 ± 309 | 1715 ± 186 | 826 ± 75 | 210 ± 31 |
| GM1 (2 μg/ml) | 2788 ± 274 | 1664 ± 191 | 837 ± 78 | 224 ± 29 |
| GM1 (5 μg/ml | 2764 ± 285 | 1728 ± 183 | 872 ± 71 | 219 ± 28 |
| peptide R4 (1 μg/ml) | 6781 ± 1549 | 4413 ± 854 | 2420 ± 561 | 1017 ± 182 |
| peptide R4 (2 μg/ml) | 15383 ± 2194 | 10375 ± 1708 | 7934 ± 1031 | 2742 ± 751 |
| peptide R4 (5 μg/ml) | 18692 ± 2310 | 12657 ± 1624 | 8354 ± 957 | 3058 ± 568 |
| peptide R1 (1 μg/ml) | 3218 ± 716 | 1876 ± 281 | 949 ± 136 | 225 ± 38 |
| peptide R1 (2 μg/ml) | 3417 ± 542 | 1864 ± 327 | 845 ± 147 | 220 ± 40 |
| peptide R1 (5 μg/ml) | 3469 ± 612 | 1781 ± 285 | 901 ± 152 | 236 ± 45 |
| peptide R2 (1 μg/ml) | 2857 ± 493 | 1714 ± 239 | 745 ± 136 | 178 ± 38 |
| peptide R2 (2 μg/ml) | 2764 ± 322 | 1653 ± 286 | 694 ± 141 | 163 ± 41 |
| peptide R2 (5 μg/ml) | 2849 ± 396 | 1628 ± 245 | 748 ± 162 | 174 ± 32 |
| peptide R3 (1 μg/ml) | 5577 ± 1063 | 2986 ± 327 | 1491 ± 364 | 682 ± 120 |
| peptide R3 (2 μg/ml) | 6351 ± 1314 | 3184 ± 439 | 1527 ± 337 | 736 ± 137 |
| peptide R3 (5 μg/ml) | 7898 ± 1496 | 3652 ± 681 | 1684 ± 375 | 812 ± 151 |

The values are mean ± SE (4 wells)

INDUSTRIAL APPLICABILITY

According to the present invention, there are provided novel amino acid sequences that mimic GD3 expressing on cancerous tissue or cancer cell surfaces. The GD3-mimetized peptides of the present invention containing any one of the amino acid sequences find utility for the preparation of drugs, including diagnostic agents for cancer or cancer vaccines. The present invention provides method for treatment of cancer, method for diagnosing cancer, etc., thus contributing improvement of therapeutic effect of cancer therapy.

The invention claimed is:

1. An isolated peptide which specifically binds to an anti-GD-3 antibody and consists of SEQ ID NO:4.

2. A composition comprising the isolated peptide of claim 1 and a pharmaceutically acceptable carrier.

* * * * *

SEQUENCE LISTING

<160> NUMBER OF SEQ ID NOS: 10

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: synthetic peptide

```
<400> SEQUENCE: 1

Leu Ala Pro Pro Arg Pro Arg Ser Gln Leu Val Phe Leu Ser Val
1               5                   10                  15

<210> SEQ ID NO 2
<211> LENGTH: 15
<212> TYPE: PRT
<213> ORGANISM: ARTIFICIAL SEQUENCE
<220> FEATURE:
<223> OTHER INFORMATION: synthetic peptide

<400> SEQUENCE: 2

Pro His Phe Asp Ser Leu Leu Tyr Pro Cys Gln Leu Leu Gly Cys
1               5                   10                  15

<210> SEQ ID NO 3
<211> LENGTH: 15
<212> TYPE: PRT
<213> ORGANISM: ARTIFICIAL SEQUENCE
<220> FEATURE:
<223> OTHER INFORMATION: synthetic peptide

<400> SEQUENCE: 3

Gly Leu Ala Pro Pro Asp Tyr Ala Gln Arg Phe Phe Leu Leu Ser
1               5                   10                  15

<210> SEQ ID NO 4
<211> LENGTH: 15
<212> TYPE: PRT
<213> ORGANISM: ARTIFICIAL SEQUENCE
<220> FEATURE:
<223> OTHER INFORMATION: synthetic peptide

<400> SEQUENCE: 4

Arg His Ala Tyr Arg Ser Met Ala Gln Trp Gly Phe Leu Tyr Ser
1               5                   10                  15

<210> SEQ ID NO 5
<211> LENGTH: 45
<212> TYPE: DNA
<213> ORGANISM: ARTIFICIAL SEQUENCE
<220> FEATURE:
<223> OTHER INFORMATION: synthetic DNA

<400> SEQUENCE: 5
ctggctcctc ctcggccgcg ttctgagctg gttttcttt ctgtt                       45

<210> SEQ ID NO 6
<211> LENGTH: 45
<212> TYPE: DNA
<213> ORGANISM: ARTIFICIAL SEQUENCE
<220> FEATURE:
<223> OTHER INFORMATION: synthetic DNA

<400> SEQUENCE: 6
ccgcattttg attcgttgct gtatccttgt gagctgctgg ggtgt                      45

<210> SEQ ID NO 7
<211> LENGTH: 45
<212> TYPE: DNA
<213> ORGANISM: ARTIFICIAL SEQUENCE
<220> FEATURE:
<223> OTHER INFORMATION: synthetic DNA

<400> SEQUENCE: 7
```

-continued

```
ggtcttgctc cgccggatta tgctgagcgt ttttttcttc tttct                45
```

<210> SEQ ID NO 8
<211> LENGTH: 45
<212> TYPE: DNA
<213> ORGANISM: ARTIFICIAL SEQUENCE
<220> FEATURE:
<223> OTHER INFORMATION: synthetic DNA

<400> SEQUENCE: 8

```
cggcatgctt atcggtctat ggctgagtgg gggtttctgt attct                45
```

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: synthetic DNA

<400> SEQUENCE: 9

```
taacactgag tttcgtcacc agta                                       24
```

<210> SEQ ID NO 10
<211> LENGTH: 23
<212> TYPE: PRT
<213> ORGANISM: ARTIFICIAL SEQUENCE
<220> FEATURE:
<223> OTHER INFORMATION: synthetic peptide

<400> SEQUENCE: 10

```
Ala Asp Gly Ala Arg Gly Gly Phe Ser Asp Thr Ser Arg Thr Gly Met
1               5                   10                  15

Val Ser Val Gly Ala Ala Gly
            20
```